United States Patent [19]

Siren

[11] Patent Number: 4,851,560
[45] Date of Patent: * Jul. 25, 1989

[54] INOSITOL TRIPHOSPHATES

[76] Inventor: Matti Siren, Via Poporino 9, CH-6926 Montagnola/Lugano, Switzerland

[*] Notice: The portion of the term of this patent subsequent to Oct. 11, 2005 has been disclaimed.

[21] Appl. No.: 15,699

[22] Filed: Feb. 17, 1987

Related U.S. Application Data

[63] Continuation-in-part of Ser. No. 788,829, Oct. 18, 1985, Pat. No. 4,777,134.

[30] Foreign Application Priority Data

Oct. 23, 1984 [SE] Sweden ................. 8405295

[51] Int. Cl.$^4$ .................. A61K 31/66; C12P 7/02
[52] U.S. Cl. ..................... 558/155; 435/155; 252/400.2
[58] Field of Search ............ 435/155; 558/155; 252/400.2

[56] References Cited

U.S. PATENT DOCUMENTS 2,723,938 11/1955 Buckwalter et al. ............. 514/103
3,591,665 7/1971 Kimura et al. ............... 252/400.2 X

OTHER PUBLICATIONS

P. E. Lim et al., Properties of Phytase Fractions F$_1$ and F$_2$ from Wheat Bran and the Myo–Inositol Phosphates Produced from Fraction F$_2$, Biochimica et. Biophysica Acta, 302 (1973), 316–328.
Tomlinson et al, Biochemistry, vol. 1, No. 1, pp. 166–171 (Jan. 1962).
Kerr et al, Archives of Biochemistry and Biophysics, vol. 96, pp. 347–353 (1962).
Biochem. and Biophys. Res. Comm., vol. 120, No. 2, 481–485 (Apr. 30, 1984).
Nature, vol. 306, 67–69 (Nov. 1983).

Primary Examiner—Thomas G. Wiseman
Assistant Examiner—Charles L. Patterson, Jr.
Attorney, Agent, or Firm—Scully, Scott, Murphy & Presser

[57] ABSTRACT

The disclosure of the present invention is directed to an inositol triphosphate compound, useful as a pharmaceutical agent, having the structural formula

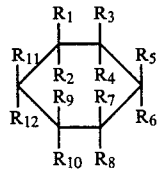

where
(a) three of $R_1$, $R_3$, $R_5$, $R_7$, $R_{10}$ and $R_{11}$ are hydroxyl and the remaining three are phosphate and $R_2$, $R_4$, $R_6$, $R_8$, $R_9$ and $R_{12}$ are hydrogen;
(b) three of $R_1$, $R_3$, $R_6$, $R_7$, $R_9$ and $R_{12}$ are hydroxyl and the remaining three are phosphate and $R_2$, $R_4$, $R_5$, $R_8$, $R_{10}$ and $R_{11}$ are hydrogen;
(c) three of $R_1$, $R_3$, $R_5$, $R_8$, $R_{10}$ and $R_{12}$ are hydroxyl and the remaining three are phosphate and $R_2$, $R_4$, $R_6$, $R_7$, $R_9$ and $R_{11}$ are hydrogen;
(d) three or $R_1$, $R_4$, $R_5$, $R_8$, $R_9$ and $R_{12}$ are hydroxyl and the remaining three are phosphate and $R_2$, $R_3$, $R_6$, $R_7$, $R_{10}$ and $R_{11}$ are hydrogen;
(e) three of $R_1$, $R_3$, $R_6$, $R_8$, $R_9$ and $R_{12}$ are hydroxyl and the remaining three are phosphate and $R_2$, $R_4$, $R_5$, $R_7$, $R_{10}$ and $R_{11}$ are hydrogen;
(f) three of $R_1$, $R_3$, $R_6$, $R_7$, $R_{10}$ and $R_{12}$ are hydroxyl and the remaining three are phosphate and $R_2$, $R_4$, $R_5$, $R_8$, $R_9$ and $R_{11}$ are hydrogen;
(g) three of $R_1$, $R_3$, $R_5$, $R_8$, $R_{10}$ and $R_{11}$ are hydroxyl and the remaining three are phosphate and $R_2$, $R_4$, $R_6$, $R_7$, $R_9$ and $R_{12}$ are hydrogen; or
(h) three of $R_1$, $R_3$, $R_5$, $R_7$, $R_9$ and $R_{11}$ are hydroxyl and the remaining three are phosphate and $R_2$, $R_4$, $R_6$, $R_8$, $R_{10}$ and $R_{12}$ are hydrogen.

21 Claims, 15 Drawing Sheets a = D-myo-inositol-1.2.6-triphosphate
b = L-myo-inositol-1.3.4-triphosphate

INOSITOL TRIPHOSPHATES

REFERENCE TO RELATED APPLICATION

This is a continuation-in-part of U.S. patent application, Ser. No. 788,829 filed Oct. 18, 1985, now U.S. Pat. No. 4,777,134, Oct. 11, 1988.

FIELD OF THE INVENTION

The present invention relates to a special inositoltriphosphate ($IP_3$), a method of producing the same and a composition containing the same.

BACKGROUND OF THE INVENTION

Even as early as the year 1900, different researchers had reported the finding of the organic phosphate compound phytic acid, i.e., 1,2,3,4,5,6-hexakis (dihydrogenphosphate) myo-inositol (also sometimes called inositolhexaphosphoric acid) in plants. The content of phytic acid in different plants varies considerably. The content in grain is usually approximately 0.5–2%, with certain exceptions. Polished rice has a level of only 0.1% while wild rice contains as much 2.2% phytic acid. Beans contain about 0.4–2%, oil plants approximately 0.2–5% and pollen 0.3–2% The content of phytic acid in the plant varies during the growth period. The content is also influenced by, among other things, the climate.

In the literature there are reports on the presence of inositol pentaphosphate ($IP_5$) and inositol tetraphosphate ($IP_4$) in a few plants. It is further known that phosphate derivates lower than $IP_6$ are formed at germination of grain. For instance the final products at the germination are inositol and phosphate. The use of $IP_6$ has been described in several scientific publications. The majority of the authors of these articles have observed several negative effects on humans and animals when consuming $IP_6$ or substances containing $IP_6$. Feeding dogs too high amount of $IP_6$ gives rise for example to rachitis. In humans lack of zinc and as a consequence thereof slower growth of children has been observed. Anemia has been observed mainly in women. Because of the above mentioned negative effects on the mineral balance in humans and animals, attempts have so far been made to reduce the intake of $IP_6$ and its derivatives to a minimum.

Furthermore, it is known for instance from Bull. Ste. Chim. Biol. 36,9 (1956) p. 85 to hydrolyse phytic acid with diluted hydrochloric acid at an increased temperature to obtain a mixture of lower inositolphosphates, i.e. $IP_5$, $IP_4$, $IP_3$, $IP_2$ (inositoldiphosphate) and $IP_1$ (inositolmonophosphate). Each of these inositolphosphates can be present in the form of many isomers. Up to 20 isomers can be expected for $IP_3$.

One specific isomer of $IP_3$, i.e. D-myo-inositol-1.4.5-triphosphate has been reported in Biochem. Biophys. Res. Commun. 120,2 (1984), page 481. This compound is known as an intracellular calcium mobilizer in the human body and it can readily be isolated from cell membranes.

Nothing is known about the properties of any other of the specific isomers of the different inositoltriphosphates in pure form. Thus, it is so difficult to separate the large number of $IP_3$ isomers from each other, thereby identify and define the structural formula of each isomer and its properties. Up to the present there is no known method for producing or obtaining any single isomer of $IP_3$ other than the aforementioned D-myo-inositol-1.4.5.-triphosphate. Further in a process for the production of $IP_3$ which includes a hydrolytic system, a re-arrangement of the isomers and/or a further dephosphorylation to $IP_2$, $IP_1$ or inositol must be considered as special problems.

Due to above difficulties there are no data on specific $IP_3$ isomers in substantially pure form other than the above-mentioned D-myo-inositol-1.4.5-triphosphate.

SUMMARY OF THE INVENTION

According to the present invention it has quite unexpectedly been possible to solve the above problem of separating certain different isomers of $IP_3$ from each other and produce them in substantially pure form. The $IP_3$ isomers can be obtained as a salt or as an acid thereof. The salt form is preferred, since it is easier to produce in pure and concentrated form than the acid.

DETAILED DESCRIPTION OF PREFERRED EMBODIMENT

Figure 1:
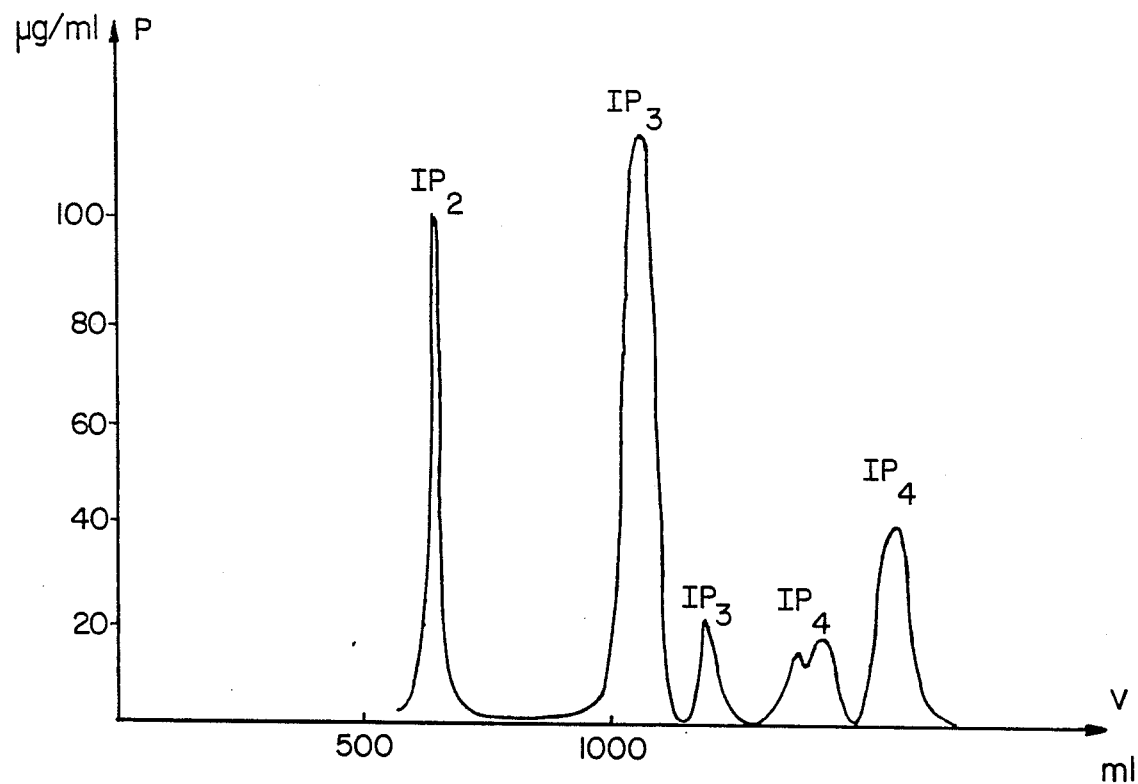

According to the invention an inositoltriphosphate ($IP_3$) selected from the group consisting of D-myo-inoistol-1.2.6-triphosphate, D-myo-inositol-1.2.5-triphosphate, L-myo-inositol-1.3.4-triphosphate and myo-inositol-1.2.3-triphosphate in either acid or salt form has been produced and isolated in substantially pure form.

As mentioned above the individual $IP_3$ isomer can be obtained as a salt or an acid thereof. In both forms it can for the first time be obtained in substantially pure form.

The $IP_3$ in acid form is generally provided in the form of an aqueous solution. In such a case the concentration of the acid may be from 10 to 45, preferably 15 to 45 or most preferably 20 to 45% by weight of the total weight of the solution.

The salt form of the $IP_3$ isomer is readily obtainable from the acid form using standard procedures. Thus, there can be prepared salts such as alkali metal and alkaline earth metal salts e.g. lithium, sodium, potassium, calcium or magnesium. However, also the aluminium, zinc and iron salts are very useful as well as the $NH_4^+$ and organic amine salts. Moreover, mixed salts containing different cations can be used.

Exemplary amines are triethanolamine, diethanolamine, triisopropanolamine, N,N-dimethyl-2-amino-2-methyl-1-propanol, N,N-dimethyl-ethanolamine, tetrabutylamine and cyclohexylamine. Also other salts might be useful. Especially preferred are salts which are physiologically acceptable.

For production of the isomer or isomers of $IP_3$ according to the invention, one or more of the compounds $IP_6$, $IP_5$ or $IP_4$ or a natural product containing at least one of these compounds can be used as a starting material. It is preferred to use $IP_6$ containing materials, since they are most easily available. In the cases where the starting material is a natural product, one with a content of at least 0.3%, preferably at least 1% by weight of inositolphosphate ($IP_6+IP_5+IP_4$) is preferably chosen.

Especially suitable products are grain, particularily bran, pollen, beans and oil plants. These products all contain $IP_6$.

In theory the $IP_3$ isomers are believed to be producible by for example the following techniques.

(1) enzymatic breakdown starting from $IP_4$, $IP_5$ and/or $IP_6$.

(2) chemical hydrolysis starting from $IP_4$, $IP_5$ and/or $IP_6$.

(3) chemical synthesis starting, for example, with inositol, $IP_1$, $IP_2$ and phosphate.

(4) enzymatic synthesis starting, for example, with inositol, $IP_1$, $IP_2$ and phosphate.

(5) microbiological production (including also hybrid DNA-techniques).

(6) chemical or enzymatic migration of inositolphosphate or chemical or enzymatic hydrolysis of substituted inositolphosphate.

Combination of two or more of the above mentioned procedures may also be possible. However many of these procedures produce only mixtures of a number of isomers which are at best extremely difficult to separate to individual isomers, if separable at all.

According to the invention a procedure where a material containing $IP_6$ is used is preferred as mentioned before. Then $IP_6$ is broken down enzymatically to $IP_3$ with phytase enzyme. Phytase enzyme is normally present in all inositolphosphate containing plants and seeds. Because of this it is, according to the invention, usually not necessary to add the enzyme if a natural product is used as starting material. In the cases where the natural product has too low an enzymatic activity or when $IP_6$, $IP_5$ or $IP_4$ or a mixture of these is used as starting material, a phytase enzyme from bran, for example, is added.

Phytase enzyme from plants, seeds and microorganisms has the surprising effect to make it possible, according to the invention, to produce the specific $IP_3$ isomers mentioned above in high concentration and in substantially pure form.

The $IP_6$ can be provided either as pure material or in the form of an $IP_6$ containing source. A suitable way to treat a natural starting material containing $IP_6$, e.g. bran is to pre-treat it, for instance by breakage or removal of outer membrane and removal of unwanted constituents. Thereafter the material is soaked in water to make the inositolphosphate available for breaking down and to activate the enzyme. Where additional enzyme is necessary, this may be added at this stage or a later stage. The enzyme is then allowed to act for so long a time as is necessary for the intended degree of hydrolysis to be achieved.

The hydrolysis takes place at a suitable temperature, usually 20°–70° C., preferably 30°–60° C. and at a pH of 4 to 8. In order to stop the hydrolysis at the intended level the enzyme may be destroyed or inactivated, for instance by a rapid heating of the hydrolysed starting material. In order to transfer the material to a form which is stable at storage it can suitably be freeze dried.

The invention especially relates to a method of producing an inositoltriphosphate ($IP_3$) selected from the group consisting of D-myo-inositol-1.2.6-triphosphate, D-myo-inositol-1.2.5-triphosphate, L-myo-inositol-1.3.4-triphosphate and myo-inositol-1.2.3-triphosphate in either acid or salt form, wherein an $IP_6$ containing material is incubated at a temperature ranging between 20° and 70° C., preferably 30° to 50° C. and a pH of 4 to 8 with phytase until the liberation of about 30–60% usually about 50% of the total ester phosphorus has been achieved. At said stage a high proportion of the desired $IP_3$ isomer or isomers has been formed by hydrolysis of the $IP_6$ containing material.

The mixture of inositolphosphates obtained may hereafter be separated by column chromatography to isolate the $IP_3$-containing fraction. In case of chromatographic separation the said fraction is then optionally subjected to another chromatographic separation, preferably in a column. Such a separation may offer advantages if the fraction contains more than one $IP_3$ isomer. The $IP_3$ isomer or isomers are then preferably isolated in acid form. By adding a base to the acid, the $IP_3$ in salt form can be obtained, if desired.

Among the many sources of phytase useful according to this invention, yeast and most preferably baker's yeast is preferred. Swedish baker's yeast produced by Jästbolaget, Sweden as well as baker's yeast produced by Rajamäki Finland and Hefefabriken AG, Switzerland have for instance been used according to the present invention. When using such yeast it has been established very surprisingly that essentially only one isomer is obtained, namely D-myo-inositol-1.2.6-triphosphate. Of course, the use of yeast is a very valuable procedure when the said isomer only is desirable.

In accordance with present knowledge no other method will provide a single isomeric product. Usually a mixture of a lot of isomers is obtained.

The above mentioned procedure, with appropriate modifications, can be used also when one or more of the compounds $IP_6$, $IP_5$ or $IP_4$ per se are used as starting material.

In another embodiment the invention also relates to an inositolphosphate composition comprised of D-myo-inositol-1.2.6-triphosphate, and at least one of D-myo-inositol-1.2.5-triphosphate, L-myo-inositol-1.3.4-triphosphate and myoinositol-1.2.3-triphosphate in acid or salt form. The composition usually contains 20–99.5, preferably 30–99.5% by weight of said $IP_3$. The content of D-myo-inositol-1.2.6-triphosphate is in the range from 50–100%, by weight based on the total content of said inositoltriphosphates, the balance including inositolphosphates other than $IP_3$.

Sometimes it might be preferable that the $IP_3$ in the composition consists essentially of D-myo-inositol-1.2.6-triphosphate solely.

In addition to $IP_3$ the balance of the inositolphosphate composition can contain also inositoltetraphosphate ($IP_4$) and inositoldiphosphate ($IP_2$).

The composition can consist of 20–99.5%, preferably more than 60%, by weight of $IP_3$ and 80–0.5%, preferably less than 40%, by weight of other inositolphosphates. 40–85%, preferably 50–85%, by weight of said other inositolphosphates should then consist of $IP_2$ plus $IP_4$. It may be preferable that the $IP_3$ consists essentially of D-myo-inositol-1.2.6-triphosphate.

The composition sometimes contains minor amounts, e.g. less than 10%, preferably 1–8% by weight of one or more of $IP_1$, and $IP_6$ calculated on the total content of inositolphosphates in the composition.

Such type of compositions are preparable by enriching the initial fermentation inositolphosphate product by addition of the D-myo-inositol-1.2.6-triphosphate to the desired final concentration of the said isomer in the composition. Such methods are well-known in the art and include e.g. simple mechanical mixing. Alternatively this composition may be produced directly by fermentation using yeast, especially baker's yeast as the phytase source. As previously indicated the use of baker's yeast results in the almost exclusive production of D-myo-inositol-1.2.6-triphosphate, i.e. substantially all of the $IP_3$ fraction is D-myo-inositol-1.2.6-triphosphate.

The inositoltriphosphate in acid or salt form according to the invention can be used as a pharmaceutical or foodstuff, optionally in additive form or as a stabilizer for various products. Moreover, $IP_3$ can give a protecting effect on seed. It can also be used as an additive for tooth-paste, as a corrosion inhibitor in paint, lacquers, lubricating oils and at surface treatment of metals, as a component in a cleansing agent, as a flame-resistant agent, for lithographic applications, for inhibition of e.g. aflatoxin production in microorganisms and for a modification or increase of the enzyme activity of amylase, for instance.

The inositol-phosphate composition produced either directly by fermentation or by enrichment as previously described is useful in all of the afore mentioned applications.

The IP$_3$-isomers mentioned above have the following formulas: D-myo-inotitol-1.2.6-triphosphate of the formula

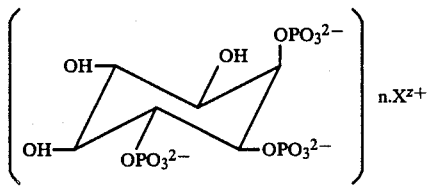

where X is hydrogen, at least one univalent, divalent or multivalent cation, or a mixture thereof, n is the number of ions, and z is the charge of the respectively ion;

D-myo-inositol-1.2.5-triphosphate of the formula

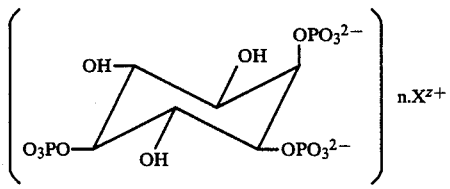

where X, n and z have the above mentioned meaning; myo-inositol-1.2.3-triphosphate of the formula

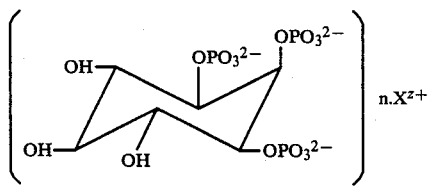

where, X, n and z have the above mentioned meaning; and

L-myo-inositol-1.3.4-triphosphate of the formula

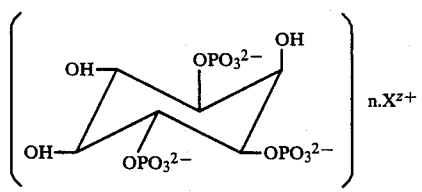

where X, n and z have the above mentioned meaning.

In each of the above formulas, n ranges between 6 to 1 inclusive and z ranges from 1 to 6 inclusive. Preferably, n is between 3 to 6 inclusive and z is 3, 2 or 1.

The new IP$_3$ isomer of the present invention are particularily effective in the afore said therapeutic use and they are especially devoid of any undesirable side-effects in this use. In particular, D-myo-inositol-1.2.6-triphosphate is especially effective and demonstrates a higher order of activity in comparison with the other isomers, especially D-myo-inositol-1.4.5-triphosphate. Complexes formed by D-myo-inositol-1.2.6-triphosphate with Cd are considerably more stable than Cd complexes formed with for example D-myo-inositol-1.4.5-triphosphate. To a lesser degree D-myo-inositol-1.2.5-triphosphate, L-myo-inositol-1.3.4-triphosphate and myo-inositol-1.2.3-triphosphate are also more desirable for therapeutic use than D-myo-inositol-1.4.5-triphosphate for many of the same reasons.

For purposes of further understanding the invention, formulas are given below of the IP$_3$ isomers of the invention. Formulas are also given for IP$_6$, IP$_5$, IP$_4$ and IP$_2$.

The lower phosphate-esters of myoinositol are named depending on where the phosphoric acid groups are situated on the inositol ring, with the numbering giving as low position numbers as possible. L and D stand for clockwise and counterclock-wise counting respectively, and are used depending on which result gives the lowest position number. The carbon atom which has an axial phosphoric acid group always has the position number 2. The structural formulae below are simplified to the acid form.

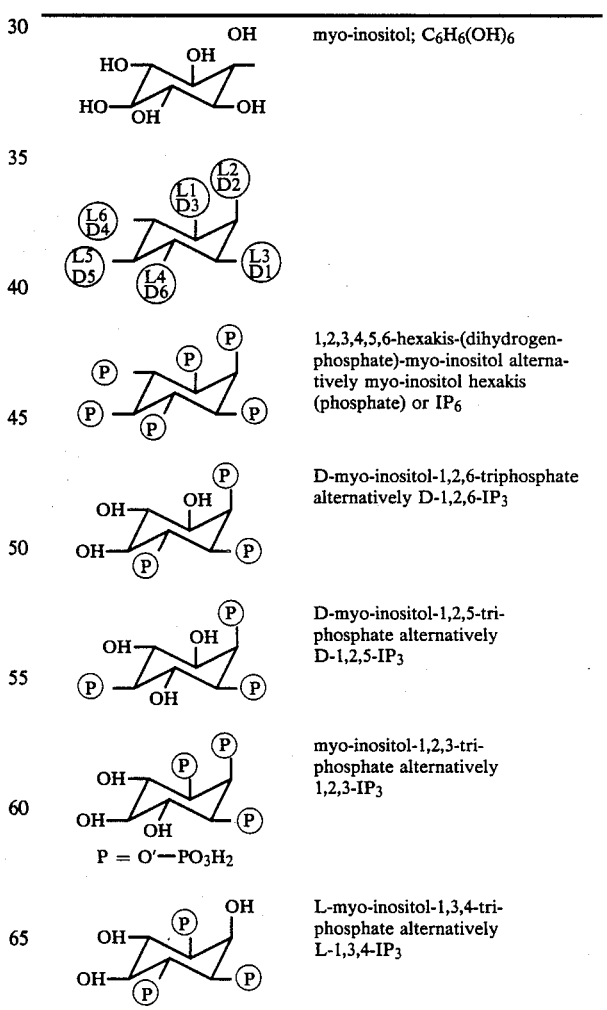

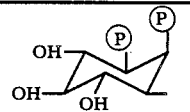

L-myo-inositol-1,2-diphos-
phate alternatively L-1,2-IP$_2$

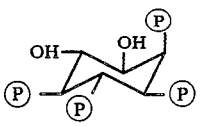

D-myo-inositol-1,2,5,6-
tetra-phosphate or D-1,2,5,
6-IP$_4$

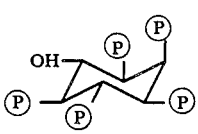

L-myo-inositol-1,2,3,4,5-
penta phosphate or
L-1,2,3,4,5-IP$_5$

P = —O—PO$_3$H$_2$

Other isomers of inositol triphosphate within the contemplation of the present invention include compounds having the structural formula

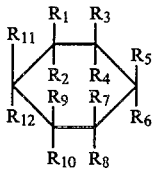

(I)

One group of inositol triphosphate compounds are defined by structural formula (I) where three of $R_1$, $R_3$, $R_5$, $R_7$, $R_{10}$ and $R_{11}$ are hydroxyl and the remaining three are phosphate and $R_2$, $R_4$, $R_6$, $R_8$, $R_9$ and $R_{12}$ are hydrogen.

Another group of inositol triphosphates are defined by structural formula (I) where three of $R_1$, $R_3$, $R_6$, $R_7$, $R_9$ and $R_{12}$ are hydroxyl and the remaining three are phosphate and $R_2$, $R_4$, $R_5$, $R_8$, $R_{10}$ and $R_{11}$ are hydrogen.

Still another group of inositol triphosphates are defined by structural formula (I) where three of $R_1$, $R_3$, $R_5$, $R_8$, $R_{10}$ and $R_{12}$ are hydroxyl and the remaining three are phosphate and $R_2$, $R_4$, $R_6$, $R_7$, $R_9$ and $R_{11}$ are hydrogen.

Yet another group of inositol triphosphates are defined by structural formula (I) where three of $R_1$, $R_4$, $R_5$, $R_8$, $R_9$ and $R_{12}$ are hydroxyl and the remaining three are phosphate and $R_2$, $R_3$, $R_6$, $R_7$, $R_{10}$ and $R_{11}$ are hydrogen.

Still yet another group of inositol triphosphates are defined by structural formula (I) where three of $R_1$, $R_3$, $R_6$, $R_8$, $R_9$ and $R_{12}$ are hydroxyl and the remaining three are phosphate and $R_2$, $R_4$, $R_5$, $R_7$, $R_{10}$ and $R_{11}$ are hydrogen.

Even still another group of inositol triphosphates are defined by structural formula (I) where three of $R_1$, $R_3$, $R_6$, $R_7$, $R_{10}$ and $R_{12}$ are hydroxyl and the remaining three are phosphate and $R_2$, $R_4$, $R_5$, $R_8$, $R_9$ and $R_{11}$ are hydrogen.

Even yet group of inositol triphosphates are defined by structural formula (I) where three of $R_1$, $R_3$, $R_5$, $R_8$, $R_{10}$ and $R_{11}$ are hydroxyl and the remaining three are phosphate and $R_2$, and $R_4$, $R_6$, $R_7$, $R_9$ and $R_{12}$ are hydrogen.

Finally, another group of inositol triphosphates are defined by structural formula (I) where three of $R_1$, $R_3$, $R_5$, $R_7$, $R_9$ and $R_{11}$ are hydroxyl and the remaining three are phosphate and $R_2$, $R_4$, $R_6$, $R_8$, $R_{10}$ and $R_{12}$ are hydrogen.

Particular inositol triphosphate compounds within the contemplation of the above groups include compounds having the structural formula (I) where $R_5$, $R_7$ and $R_{10}$ are phosphate, $R_1$, $R_3$ and $R_{11}$ are hydroxyl and $R_2$, $R_4$, $R_6$, $R_8$, $R_9$ and $R_{12}$ are hydrogen;

$R_1$, $R_{10}$ and $R_{11}$ are phosphate, $R_3$, $R_5$ and $R_7$ are hydroxyl and $R_2$, $R_4$, $R_6$, $R_8$, $R_9$ and $R_{12}$ are hydrogen;

$R_1$, $R_3$ and $R_{11}$ are phosphate, $R_5$, $R_7$ and $R_{10}$ are hydroxyl and $R_2$, $R_4$, $R_6$, $R_8$, $R_9$ and $R_{12}$ are hydrogen;

$R_3$, $R_5$ and $R_7$ are phosphate, $R_1$, $R_{10}$ and $R_{11}$ are hydroxyl and $R_2$, $R_4$, $R_6$, $R_8$, $R_9$ and $R_{12}$ are hydrogen;

$R_3$, $R_7$ and $R_{10}$ are phosphate, $R_1$, $R_5$ and $R_{11}$ are hydroxyl and $R_2$, $R_4$, $R_6$, $R_8$, $R_9$ and $R_{12}$ are hydrogen;

$R_3$, $R_{10}$ and $R_{11}$ are phosphate, $R_1$, $R_5$ and $R_7$ are hydroxyl and $R_2$, $R_4$, $R_6$, $R_8$, $R_9$ and $R_{12}$ are hydrogen;

$R_1$, $R_3$ and $R_6$ are phosphate, $R_7$, $R_9$ and $R_{12}$ are hydroxyl and $R_2$, $R_4$, $R_5$, $R_8$, $R_{10}$ and $R_{11}$ are hydrogen;

$R_6$, $R_7$ and $R_9$ are phosphate, $R_1$, $R_3$ and $R_{12}$ are hydroxyl and $R_2$, $R_4$, $R_5$, $R_8$, $R_{10}$ and $R_{11}$ are hydrogen;

$R_3$, $R_5$, and $R_8$ are phosphate, $R_1$, $R_{10}$ and $R_{12}$ are hydroxyl and $R_2$, $R_4$, $R_6$, $R_7$, $R_9$ and $R_{11}$ are hydrogen;

$R_1$, $R_3$ and $R_{12}$ are phosphate, $R_5$, $R_8$ and $R_{10}$ are hydroxyl and $R_2$, $R_4$, $R_6$, $R_7$, $R_9$ are $R_{11}$ are hydrogen;

$R_1$, $R_3$ and $R_5$ are phosphate, $R_8$, $R_{10}$ and $R_{12}$ are hydroxyl and $R_2$, $R_4$, $R_6$, $R_7$, $R_9$ and $R_{11}$ are hydrogen;

$R_1$, $R_5$ and $R_8$ are phosphate, $R_3$, $R_{10}$ and $R_{12}$ are hydroxyl and $R_2$, $R_4$, $R_6$, $R_7$, $R_9$ and $R_{11}$ are hydrogen;

$R_1$, $R_5$ and $R_{12}$ are phosphate, $R_3$, $R_8$ and $R_{10}$ are hydroxyl and $R_2$, $R_4$, $R_6$, $R_7$, $R_9$ an $R_{11}$ are hydrogen;

$R_1$, $R_3$ and $R_{12}$ are phosphate, $R_6$, $R_8$ and $R_9$ are hydroxyl and $R_2$, $R_4$, $R_5$, $R_7$, $R_{10}$ and $R_{11}$ are hydrogen;

$R_1$, $R_3$ and $R_6$ are phosphate, $R_7$, $R_{10}$ and $R_{12}$ are hydroxyl and $R_2$, $R_4$, $R_5$, $R_8$, $R_9$ and $R_{11}$ are hydrogen;

$R_4$, $R_5$ and $R_8$ are phosphate, $R_1$, $R_9$ and $R_{12}$ are hydroxyl and $R_2$, $R_3$, $R_6$, $R_7$, $R_{10}$ and $R_{11}$ are hydrogen;

$R_3$, $R_5$ and $R_8$ are phosphate, $R_1$, $R_{10}$ and $R_{11}$ are hydroxyl and $R_2$, $R_4$, $R_6$, $R_7$, $R_9$ and $R_{12}$ are hydrogen;

$R_1$, $R_3$ and $R_5$ are phosphate, $R_8$, $R_{10}$ and $R_{11}$ are hydroxyl and $R_2$, $R_4$, $R_6$, $R_7$, $R_9$ and $R_{12}$ are hydrogen;

$R_1$, $R_3$ and $R_5$ are phosphate, $R_7$, $R_9$ and $R_{11}$ are hydroxyl and $R_2$, $R_4$, $R_6$, $R_8$, $R_{10}$ and $R_{10}$ and $R_{12}$ are hydrogen;

$R_1$, $R_3$ and $R_{12}$ are phosphate, $R_5$, $R_8$ and $R_9$ are hydroxyl and $R_2$, $R_4$, $R_6$, $R_7$, $R_{10}$ and $R_{11}$ are hydrogen;

$R_1$, $R_3$ and $R_8$ are phosphate, $R_5$, $R_9$, $R_{12}$ are hydroxyl and $R_2$, $R_4$, $R_6$, $R_7$, $R_{10}$ and $R_{11}$ are hydrogen;

$R_3$, $R_5$ and $R_{12}$ are phosphate, $R_1$, $R_8$ and $R_9$ are hydroxyl and $R_2$, $R_4$, $R_6$, $R_7$, $R_{10}$ and $R_{11}$ are hydrogen;

$R_1$, $R_5$ and $R_9$ are phosphate, $R_3$, $R_8$ and $R_{12}$ are hydroxyl and $R_2$, $R_4$, $R_6$, $R_7$, $R_{10}$ and $R_{11}$ are hydrogen;

$R_1$, $R_5$ and $R_{12}$ are phosphate, $R_3$, $R_8$ and $R_9$ are hydroxyl and $R_2$, $R_4$, $R_6$, $R_7$, $R_{10}$ and $R_{11}$ are hydrogen;

$R_1$, $R_3$ and $R_9$ are phosphate, $R_5$, $R_8$ and $R_{12}$ are hydroxyl and $R_2$, $R_4$, $R_6$, $R_7$, $R_{10}$ and $R_{11}$ are hydrogen;

$R_1$, $R_8$ and $R_9$ are phosphate, $R_3$, $R_5$ and $R_{12}$ are hydroxyl and $R_2$, $R_4$, $R_6$, $R_7$, $R_{10}$ and $R_{11}$ are hydrogen;

$R_1$, $R_8$ and $R_{12}$ are phosphate, $R_3$, $R_5$ and $R_9$ are hydroxyl and $R_2$, $R_4$, $R_6$, $R_7$, $R_{10}$ and $R_{11}$ are hydrogen;

$R_5$, $R_8$ and $R_{12}$ are phosphate, $R_1$, $R_3$ and $R_9$ are hydroxyl and $R_2$, $R_4$, $R_6$, $R_7$, $R_{10}$ and $R_{11}$ are hydrogen;

$R_1$, $R_9$ and $R_{12}$ are phosphate, $R_3$, $R_5$ and $R_8$ are hydroxyl and $R_2$, $R_4$, $R_6$, $R_7$, $R_{10}$ and $R_{11}$ are hydrogen;

$R_5$, $R_8$ and $R_9$ are phosphate, $R_1$, $R_3$ and $R_{12}$ are hydroxyl and $R_2$, $R_4$, $R_6$, $R_7$, $R_{10}$ and $R_{11}$ are hydrogen;

$R_3$, $R_8$ and $R_9$ are phosphate, $R_1$, $R_5$ and $R_{12}$ are hydroxyl and $R_2$, $R_4$, $R_6$, $R_7$, $R_{10}$ and $R_{11}$ are hydrogen;

$R_3$, $R_9$ and $R_{12}$ are phosphate, $R_1$, $R_5$ and $R_8$ are hydroxyl and $R_2$, $R_4$, $R_6$, $R_7$, $R_{10}$ and $R_{11}$ are hydrogen;

$R_3$, $R_8$ and $R_{12}$ are phosphate, $R_1$, $R_5$ and $R_9$ are hydroxyl and $R_2$, $R_4$, $R_6$, $R_7$, $R_{10}$ and $R_{11}$ are hydrogen; and $R_8$, $R_9$ and $R_{12}$ are phosphate, $R_1$, $R_3$ and $R_5$ are hydroxyl and $R_2$, $R_4$, $R_6$, $R_7$, $R_{10}$ and $R_{11}$ are hydrogen.

The above discussed compounds having structural formula (I) are made by the same procedure set forth in Examples 26 to 29.

The invention will be explained further in connection with the embodiment examples below and the enclosed figures and table. Examples 1 and 2 show a hydrolysis of sodium phytate with wheat phytase and fractionation of a mixture of inositolphosphates. Examples 3 and 4 relate to structural determination of isomers of $IP_3$. Example 5 illustrates a determination of pKa-values for $IP_3$. Example 6 shows a determination of relative binding constants for $IP_3$ with Ca, Zn and Cd respectively. Examples 7-10 relate to work-up procedures for calcium salts of the $IP_3$-isomers of the invention. Example 11 illustrates the infrared spectrum of the calcium salt of D-myo-inositol-1.2.6-triphosphates. Examples 12 and 13 show a hydrolysis of sodium phytate with wheat bran and a fractionation of the mixture of inostitolphosphates obtained. Example 14 relates to a work-up procedure of the zinc salt of D-myo-inositol-1.2.6-triphosphate. Examples 15-17 show a hydrolysis of sodium phytate with baker's yeast, a fractionation of the mixture of inositolphosphates obtained and a determination of the sole isomer of $IP_3$ obtained. Example 18 illustrates a work-up procedure of the sodium salt of D-myo-inositol-1.2.6-triphosphate. Example 19 shows a chemical hydrolysis of sodium phytate with hydrochloric acid and a fractionation of the mixture of inositolphosphates obtained. Example 21 relates to a chemical synthesis of inositolphosphates from polyphosphoric acid and myo-inositol and a structural determination of the $IP_3$ with H-NMR. Example 21 shows hydrolysis of phytic acid in rice bran, extraction and analyzis of the inositolphosphates obtained. Example 22 relates to a characterization of different salts of D-myo-inositol-1.2.6-triphosphate. Example 23 shows that $IP_3$ prevents an increase of platelet aggregation in humans caused by smoking, In example 24 it is shown that an increased blood glucose level in mice caused by free radicals can be counteracted by injection of $IP_3$.

EXAMPLE 1

Hydrolysis of sodium phytate with wheat phytase and fractionation of a mixture of inositolphosphates A 1.6 gram quantity of sodium phytate (from corn, Sigma Chemical Co, St. Louis, Missouri, USA) was dissolved in 650 ml sodium acetate buffer, pH 5.2 2.7 gram wheat phytase (EC 3.1.3.26, 0.015 U/mg, from Sigma Chemical Co) was added and the mixture was incubated at 38° C.

The dephosphorylation was followed by determining the inorganic phosphorus released. After 3 hours when 50% inorganic phosphorus had been liberated the hydrolysis was stopped by adding 30 ml ammonia to pH 12. A liquid mixture containing inositolphosphates was obtained.

350 ml of the mixture was passed through an ion-exchange column (Dowex 1, chloride form, 25 mm×250 mm) and eluted with a linear gradient of hydrochloric acid (0–0.7N HCl). Aliquots of eluted fractions were completely hyrolyzed in order to determine the contents of phosphorus and inositol. The amount of phosphorus versus eluted volume is shown in FIG. 1. The peaks correspond to different inositolphosphates i.e. a peak with the ratio of phosphorus to inositol of three to one consists of inositoltriphosphate etc. Two fractions with the ratio of phosphorus to inositol of three to one were obtained.

EXAMPLE 2

Figure 2:
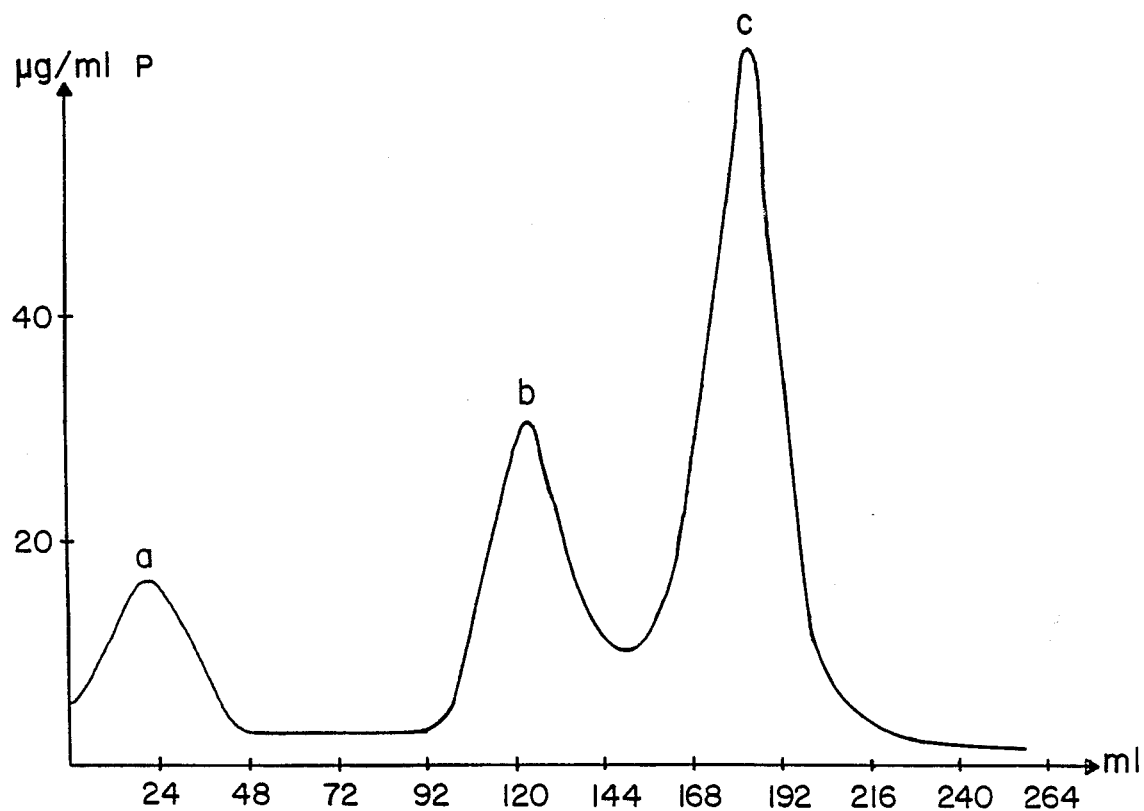

Fractionation of inositoltriphosphates 100 ml of the first fraction obtained in Example 1 with a phosphorus/inositol ratio of three to one was neutralized and precipitated as a bariumsalt after addition of 10% excess of 0.1M bariumacetate solution. 600 mg of the precipitated salt was dissolved in 50 ml 0.18N hydrochloric acid. The solution was separated on an ionexchange column (Dowex 1, chloride form, 25 mm×2500 mm) with diluted hydrochloric acid as eluent. Aliquots of eluted fractions were analyzed for phosphorus. The amount of phosphorus versus eluted volume is shown in FIG. 2. Three peaks consisting of isomers of inositoltriphosphates can be seen in the figure.

EXAMPLE 3

Structural determination of isomers of inositoltriphosphates with H-NMR.

Figure 3A:
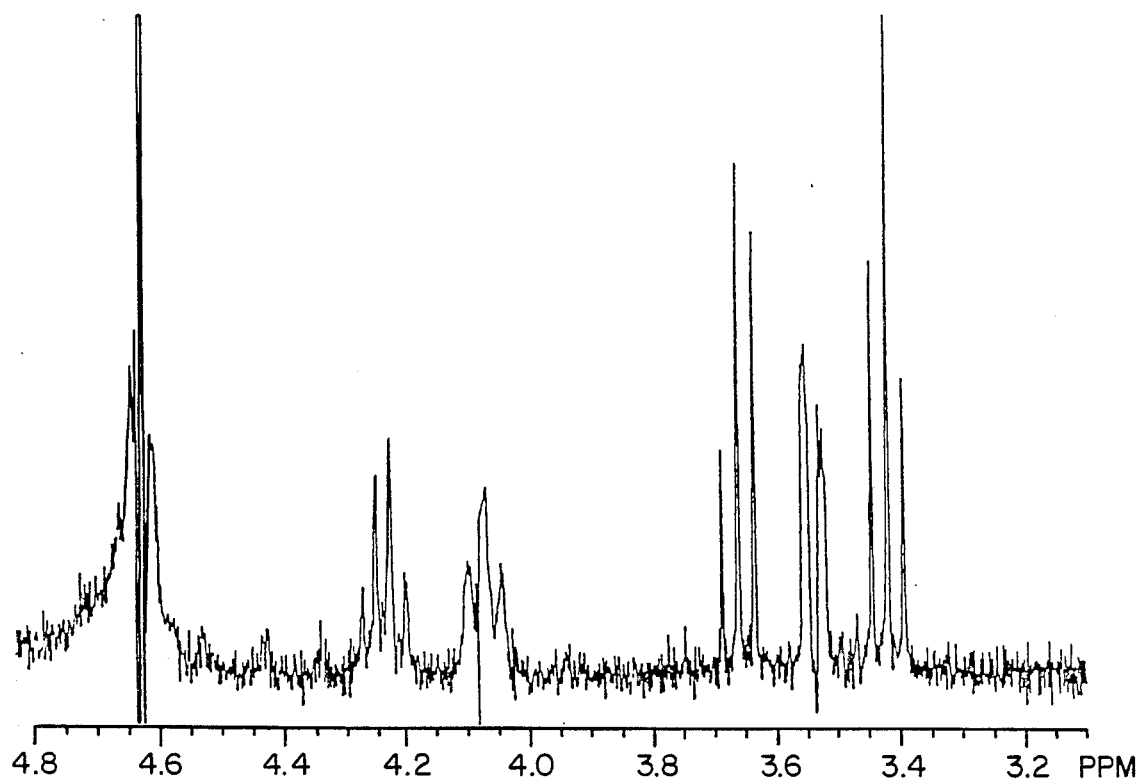
Figure 3B:
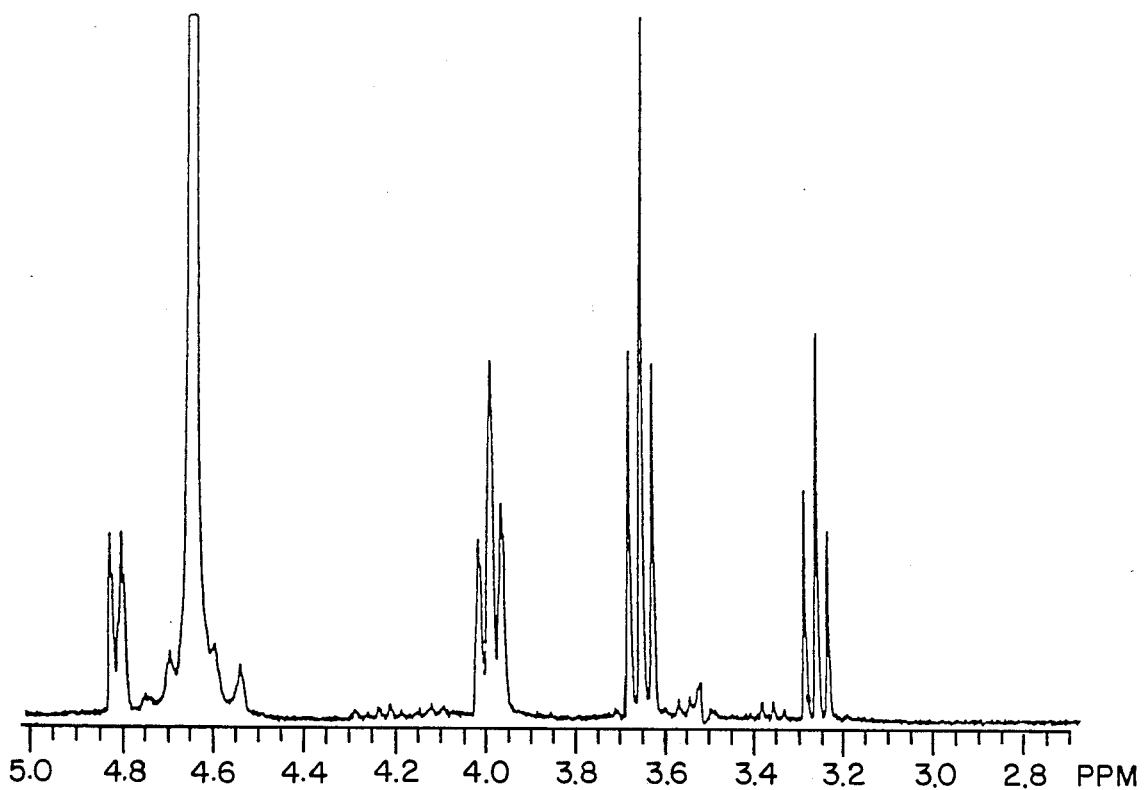
Figure 3C:
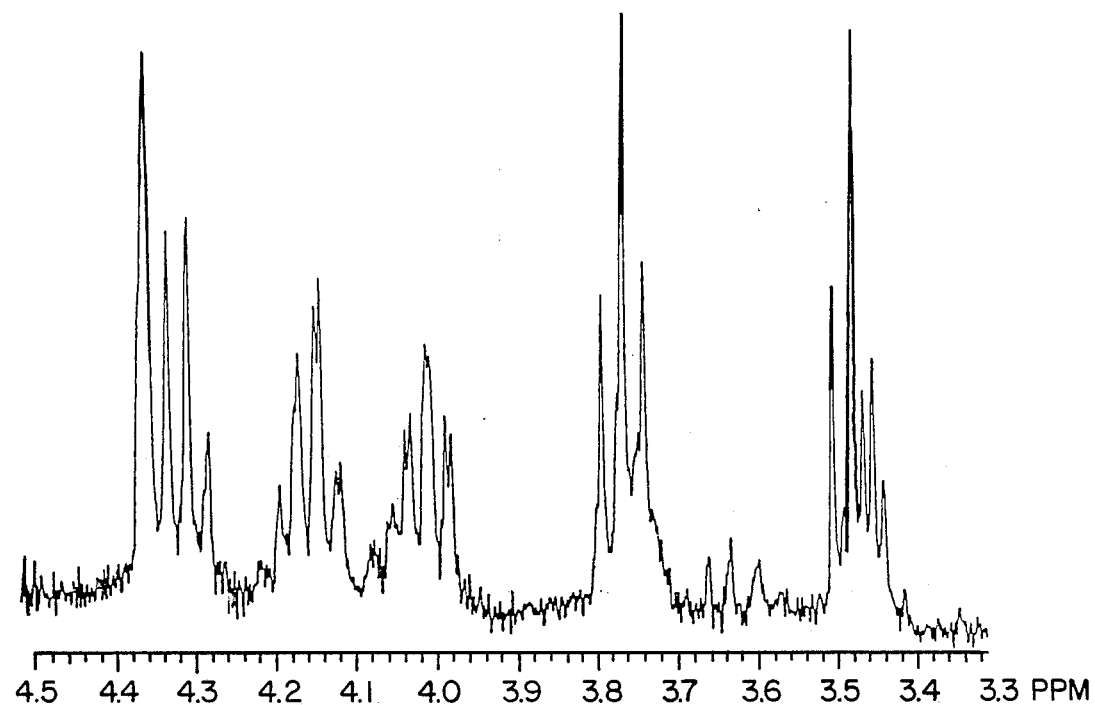

The three peaks obtained in Example 2 were analyzed by H-NMR. The spectra are shown in FIG. 3 $a$, $b$ and $c$. Data show that the peaks consist of myo-inositol-1.2.8-triphosphate, myo-inositol-1.2.3-triphosphate and myo-inositol-1.3.4-triphosphate respectively.

Figure 4:
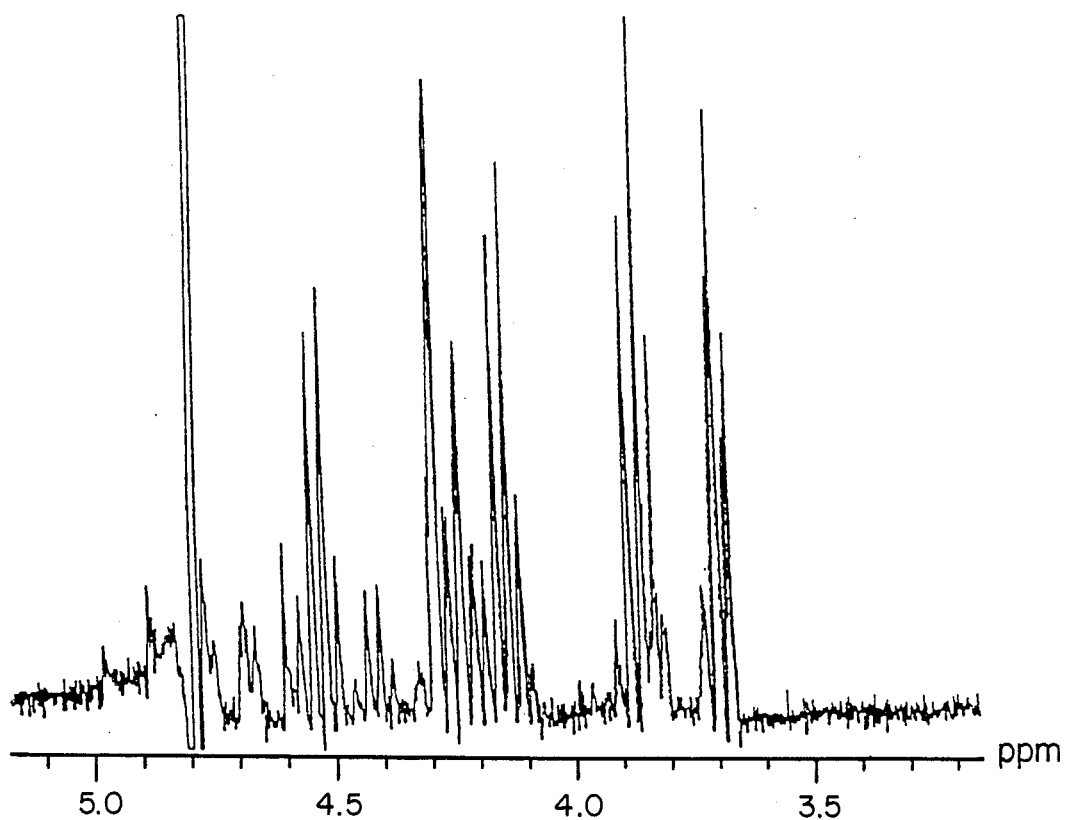

The second fraction obtained in Example 1 with a phosphorous/inositol ratio of three to one was analyzed by H-NMR. The spectrum is shown in FIG. 4. Data show that the fraction consists of myo-inositol-1.2.5-triphosphate. In this embodiment example as well as in all the following ones where H-NMR was used, the H-NMR instrument was a Nicolet 360 WB spectrometer. The internal standard was tetramethylsilane.

EXAMPLE 4

Figure 5:
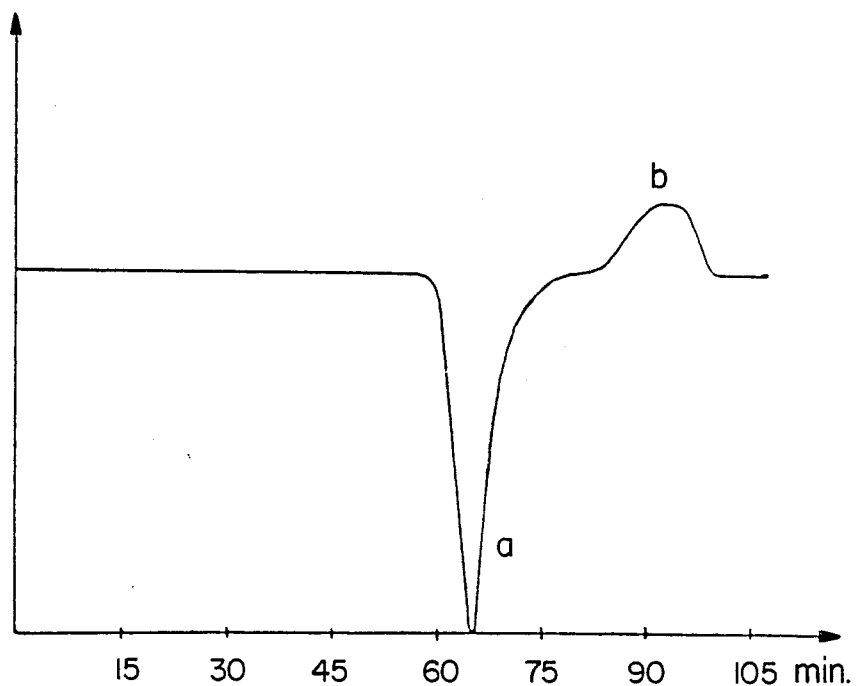

Determination of optical isomers of inositoltriphosphates 20 mg of the compounds determined with H-NMR according to Example 3 to be myo-inositol-1.2.6-triphosphate and myo- inositol-1.3.4-triphosphate were further chromatographed on a chiral column based on acetylated cellulose (20 mm×300 mm from Merck) with a mixture of ethanol and water as eluent. The fractions were analyzed with a polarimeter. As can be seen in FIG. 5 each compound consists of one optical isomer, D-myo-inositol-1.2.6-triphosphate and L-myo-inositol-1.3.4-triphosphate respectively.

EXAMPLE 5

Determination of pKa-values for inositoltriphosphates

Figure 6:
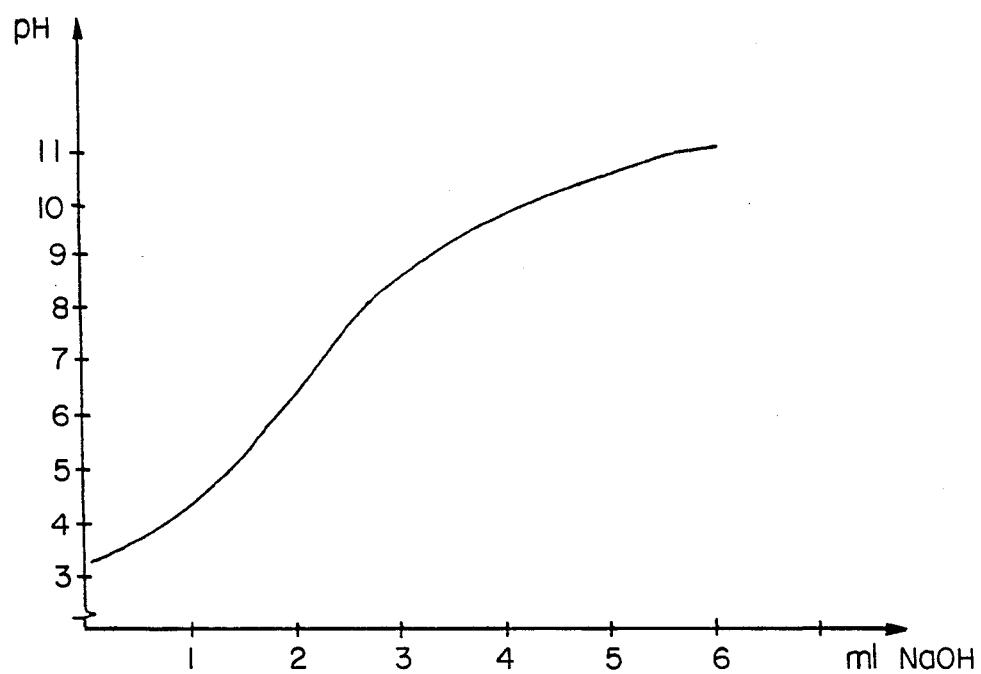

A 10 ml quantity of the first fraction obtained in Example 1 with a phosphorus/inositol ratio of three to one was titrated with 0.01M NaOH. The pH during the titration was measured with an electrode. FIG. 6 shows the pH versus volume NaOH.

The following pKa-values were obtained:

pKa1=4.7 pKa2=7.5

EXAMPLE 6

Figure 7:
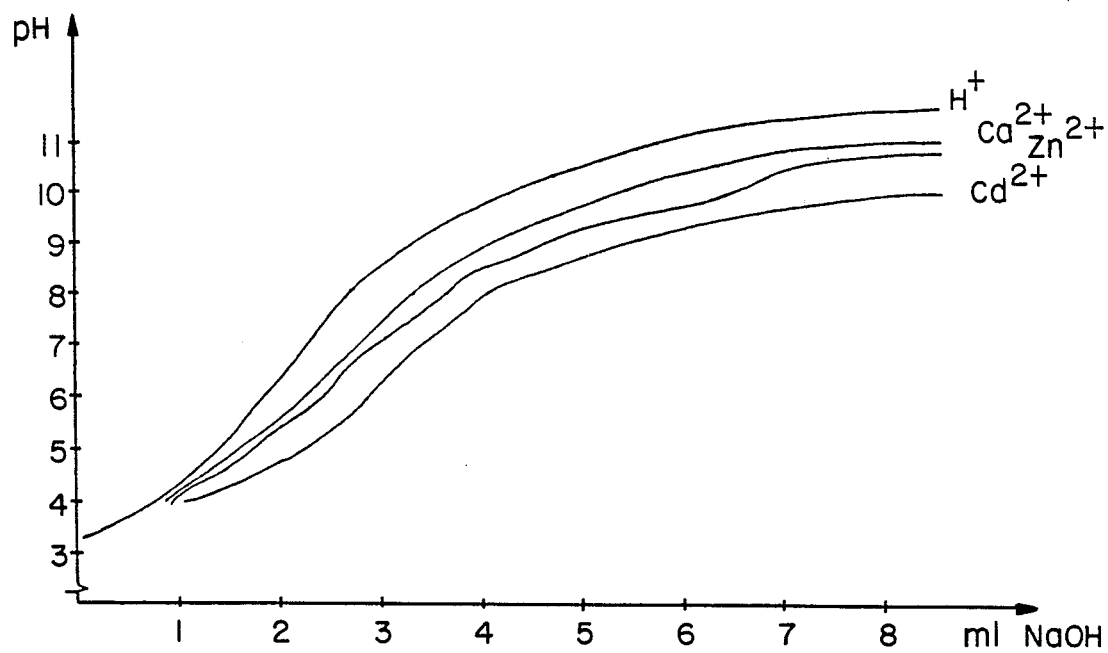

Determination of relative binding constants for inositoltriphosphates and calcium, zinc and cadmium respectively A 10 ml quantity of the first fraction obtained in Example 1 with a phosphorus/inositol ratio of three to one was titrated with 0.01 M NaOH in the presence of 0.2 mM calcium, zinc and cadmiumions respectively. A greater tendency to formation of an inositoltriphosphate-metalcomplex results in lowering the pH at a certain volume NaOH added. As can be seen in FIG. 7 the metal binding constants for $IP_3$ increase in the following order:

Ca<Zn<Cd

EXAMPLE 7

Work-up procedure of calciumsalt of D-myo-inositol-1.2.6-triphosphate 100 ml of the fraction containing D-myo-inositol-1.2.6-triphosphate obtained in Example 2 was neutralized to a pH of about 7 with an aqueous solution of 100 ml ethanol. The precipitate was centrifuged recrystallized and dried in vacuum.

The purified calciumsalt of D-myo-inositol-1.2.6-triphosphate obtained was structurally confirmed by analysis with H-NMR.

The above recrystallized calciumsalt of D-myo-inositol-1.2.6-triphosphate was also chemically analyzed in order to determine the content of carbon phosphorus, oxygen and calcium. Table 1 shows the result. The formula of the salt is $Ca_3IP_3$.

EXAMPLE 8

Work-up procedure of calciumsalt of L-myo-inositol-1.3.4-triphosphate 100 ml of the fraction containing L-myo-inositol-1.2.4-triphosphate obtained in Example 2 was neutralized to a pH of about 7 with an aqueous solution of $Ca(OH)_2$. The calciumsalt was precipitated by the addition of 100 ml ethanol. The precipitate was centrifuged, recrystallized and dried in vacuum.

The purified calciumsalt of L-myo-inositol-1.3.4-triphosphate was structurally confirmed by analysis with H-NMR.

The above recrystallized calciumsalt of L-myo-inositol-1.3.4-triphosphate was also chemically analyzed in order to determine the content of carbon phosphorous, oxygen and calcium. Table 1 shows the result. The formula of the salt is $Ca_3IP_3$.

EXAMPLE 9

Work-up procedure of calciumsalt of myo-inositol-1.2.3-triphosphate 100 ml of the fraction containing myo-inositol-1.2.3-triphosphate obtained in Example 2 was neutralized to a pH of about 7 with an aqueous solution of $Ca(OH)_2$. The calciumsalt was precipitated by the addition of 100 ethanol. The precipitate was recrystallized and dried in vacuum.

The purified calciumsalt of myo-inositol-1.2.3-triphosphate was structurally confirmed by anlysis with H-NMR.

The above recrystallized calciumsalt of myo-inositol-1.2.3-triphosphate was also chemically analyzed in order to determine the content of carbon, phosphorus, oxygen and calcium. Table 1 shows the result. The formula of the salt is $Ca_3IP_3$.

EXAMPLE 10

Work-up procedure of calciumsalt of D-myo-inositol-1.2.5-triphosphate 100 ml of the fraction containing D-myo-inositol-1.2.5-triphosphate obtained in Example 1 was neutralized to a pH of about 7 with an aqueous solution of $Ca(OH)_2$. The calciumsalt was precipitated by the addition of 100 ml ethanol. The precipitate was centrifuged, recrystallized and dried in vacuum.

The purified calciumsalt of D-mayo-inositol-1.2.5-triphosphate was structurally confirmed by analysis with H-NMR.

The above recrystallized calciumsalt of D-myo-inositol-1.2.5-triphosphate was also chemically analyzed in order to detemine the content of carbon, phosphorus, oxygen and calcium. Table 1 shows the result. The formula of the salt is $Ca_3IP_3$.

EXAMPLE 11

Infrared (IR) spectrum of the calciumsalt of D-myo-inositol-1.2.6-triphosphate

The purified calciumsalt of D-myo-inositol-1.2.6-triphosphate obtained in Example 7 was analyzed with IR. The characteristic bands are:

3500 cm$^{-1}$-OH 2900 cm$^{-1}$-CH 1600 cm$^{-1}$-OH 1100 cm$^{-1}$-C—O and —P 1000 cm$^{-1}$-C—O and —P 800 cm$^{-1}$-C—C

EXAMPLE 12

Hydrolysis of sodium phytate with wheat bran and fractionation of a mixture of inositolphosphates A 10 gram quantity of sodium phytate (from corn Sigma Chemical Co) was dissolved in 500 ml sodium acetate, buffer at pH 5.0. With the temperature increased to 37° C., wheat bran (10 g) was added at stirring. Incubation was started and continued at 37° C. The dephosphorylation was followed by determining the inorganic phosphorus released. The hydrolysis was stopped by addition of 100 ml ammonia after 2 hours when 50% inorganic phosphorus had been liberated. The suspension obtained was centrifuged and the supernatant was collected.

300 ml of the supernatant was passed through an ion-exchange column (Dowex 1, chloride form, 25 mm×250 mm) and eluted with a linear gradient of hydrochloric acid (0–0.7 N HCl). Aliquots of eluted fractions were completely hydrolyzed in order to determine the contents of phosphorus and inositol. Two fractions with the phosphorous/inositol ratio of three to one (IP3) were collected.

EXAMPLE 13

Fractionation of inositoltriphosphates

The same method was used as described in Example 2 except for the difference that the first fraction collected in Example 12 was chromatographed. Three peaks were obtained and analyzed by H-NMR. The peaks consist of myo-inositol-1.2.6-triphosphate, myo-inositol-1.2.3-triphosphate and myo-inositol-1.3.4-triphosphate respectively.

EXAMPLE 14

Work-up procedure of the zincsalt of D-myo-inositol-1.2.6-triphosphate 100 ml of the fraction containing D-myo-inositol-1.2.6-triphosphate obtained in Example 13 was neutrilized to a pH of about 7 with an aqueous solution of ZnO. The zincsalt was precipitated at the addition of 100 ml ethanol. The precipitate was centrifuged, recrystallized and dried in vacuum. The above recrystallized zincsalt of D-myo-inostiol-1.2.6-triphosphate was also chemically analyzed in order to determine the content of carbon, phosphorus, oxygen and zinc. Table 1 shows the result. The formula of the salt is $Zn_3IP_3$.

EXAMPLE 15

Figure 8:
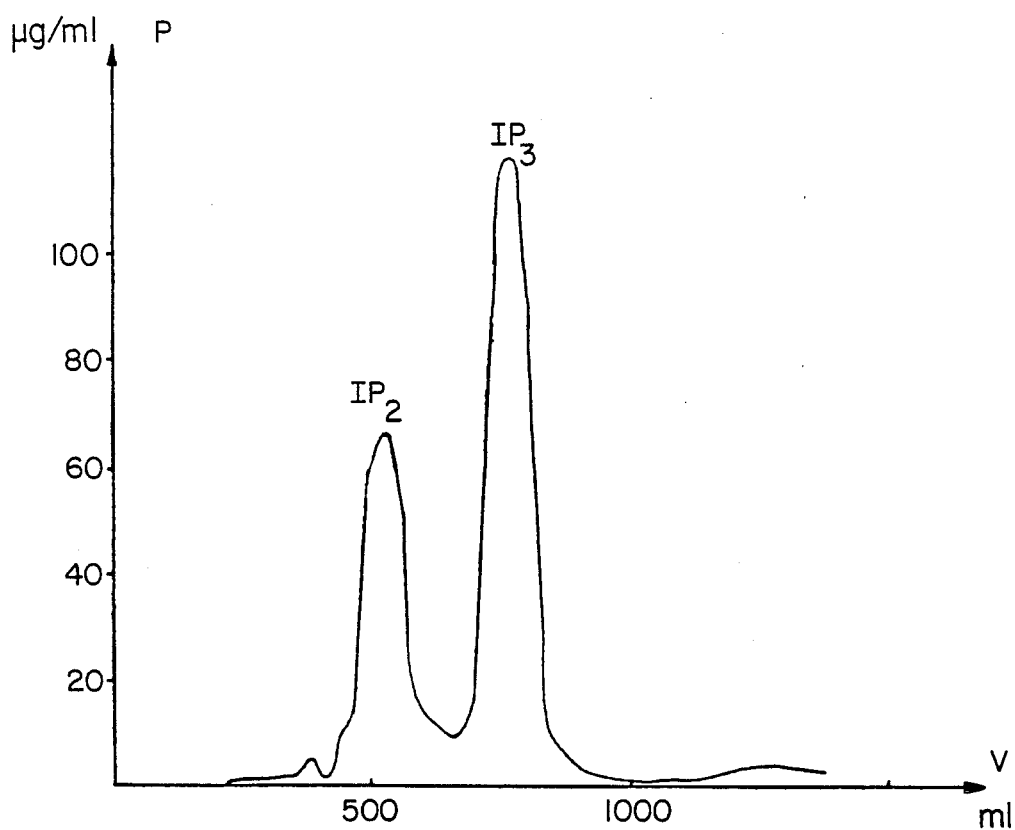

Hydrolysis of sodium phytate with baker's yeast and fractionation of a mixture of inositolphosphates A 0.7 gram quantity of sodium phytate (from corn, Sigma Chemical Co) was dissolved in 600 ml sodium acetate buffer at pH 4.6 50 gram of baker's yeast from Jästbolaget, Sweden (solid contents 28%, nitrogen content 2%, phosphorus content 0.4%) was added at stirring. Incubation was started and continued at 45° C. The dephosphorylation was followed by determining the inorganic phosphorus released. After 7 hours when 50% inorganic phosphorus had been liberated the hydrolysis was stopped by adding 30 ml of ammonia to pH 12. The suspension was centrifuged and the supernatant was collected. 400 ml of the supernatant was passed through an ion-exchange column (Dowex 1, chloride from, 25 mm×250 mm) and eluted with a linear gradient of hydrochloric acid (0–0.7 N HCl). Aliquots of eluted fractions were completely hydrolyzed in order to determine the contents of phosphorus and inositol. The amount of phosphorus versus eluted volume, is shown in FIG. 8. The peaks correspond to different inositolphosphates i.e. a peak with the ratio of phosphorus to inositol of three to one consists of inositoltriphosphates etc.

EXAMPLE 16

Structural determination of isomers of inositoltriphosphate

The fraction obtained in Example 15 with a phosphorus/inositol ratio of three to one was neutralized and evaporated before analysis with H-NMR. The spectrum proved to be identical with that shown in FIG. 3a. Data show that the peak consists of myo-inositol1.2.6-triphosphate.

EXAMPLE 17

Determination of optical isomers of myo-inositol-triphosphate

Figure 9:
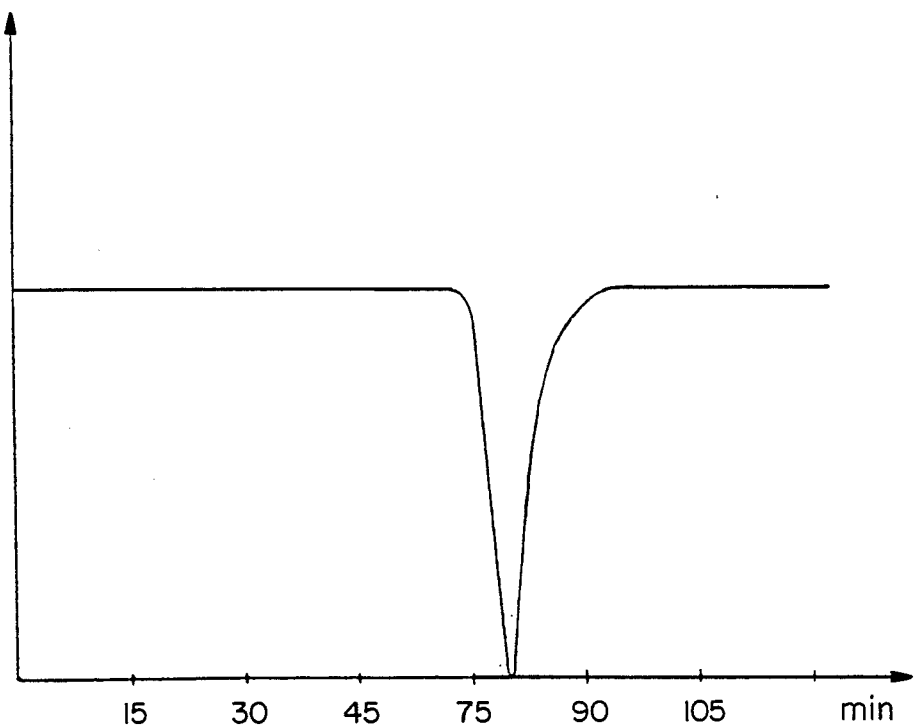

The same method was used as described in Example 4 with the difference that 10 mg of the compound determined with NMR according to Example 16 was analyzed. As can be seen in FIG. 9 the compound consists of one optical isomer, D-myo-inositol-1.2.6-triphosphate. Said isomer can be rearranged to L-myo-inositol-1.3.4-triphosphate by treatment with an acid such as hydrochloric acid.

EXAMPLE 18

Work-up procedure of the sodiumsalt of D-myo-inositol-1.2.6-triphosphate.

100 ml of the fraction containing D-myo-inositol-1.2.6-triphosphate obtained in Example 15 was neutralized to a pH of about 7 with an aqueous solution of NaOH. After addition of 100 ml ethanol the volume of the solution was reduced by evaporation and the sodiumsalt was precipitated, centrifuged, recrystallized and dried in vacuum. The purified sodiumsalt of D-myo-inositol-1.2.6-triphosphate obtained was structurally confirmed by analysis with H-NMR.

The recrystallized sodiumsalt of D-myo-inositol-1.2.6-triphosphate was chemically analyzed in order to determine the contents of carbon, phosphorous, oxygen and sodium. Table 1 shows the result. The formula of the salt is $Na_6IP_3$.

EXAMPLE 19

Chemical hydrolysis of sodium phytate and fractionation of a mixture of inositolphosphates A 1.0 gram quantity of sodium phytate (from corn, Sigma Chemical Co) was dissolved in 15 ml 6 N HCl. The sample was heated under vacuum in a sealed tube in an oven (105° C.) for 5 hours. After this time 34% of inorganic phosphorous had been released.

Figure 10:
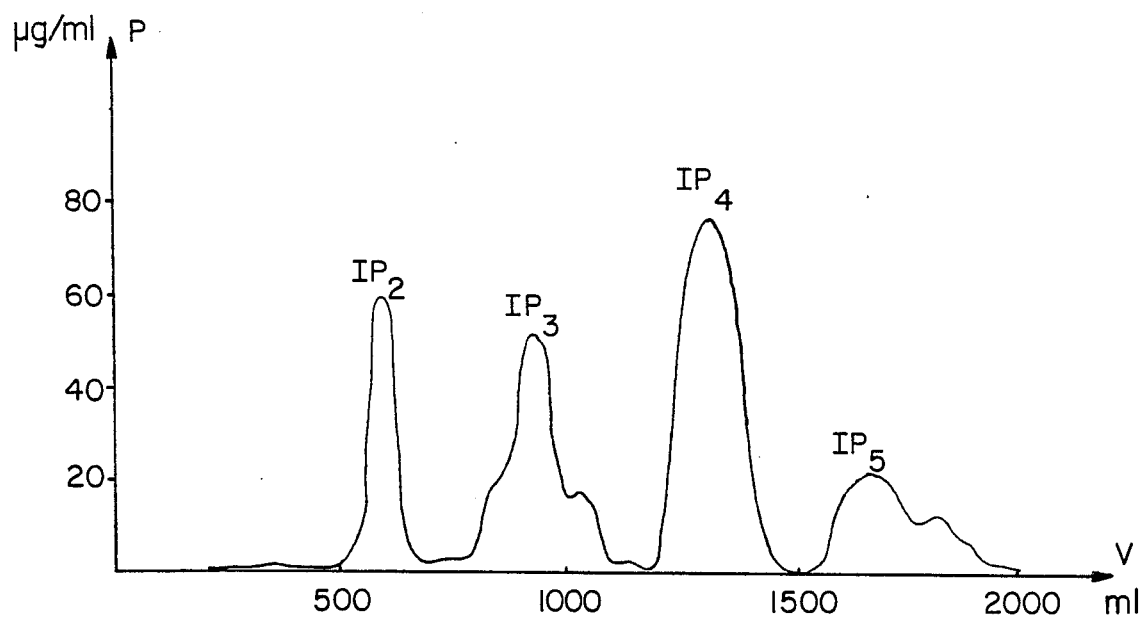

5 ml of the liquid mixture was neutralized to pH 7 with an aqueous solution of NaOH and passed through an ionexchange column (Dowex 1, chloride form 10 mm×150 mm) and eluted with a linear gradient of hydrochloric acid (0–0.7 N HCl). Aliquots of eluted fractions were completely hydrolyzed in order to determine the contents of phosphorus and inositol. The amount of phosphorus versus eluted volume is shown in FIG. 10. The fraction with the ratio of phosphorus to inositol of three to one was collected. The H-NMR spectrum indicated a substantial number of isomeric products.

EXAMPLE 20

Chemical synthesis of inositolphosphates

Polyphosphoric acid (80% $P_2O_5$, 3.5 g) was introduced into a glass-stoppered flask and heated to 150° C. Myoinositol, 0.2 g, was added and the mixture maintained at said temperature for 2 hours until it was neutralized to pH 7 with an aqueous solution of NaOH. The composition obtained was precipitated as a bariumsalt after addition of 10 % excess of 0.1 M bariumacetate solution.

Figure 11:
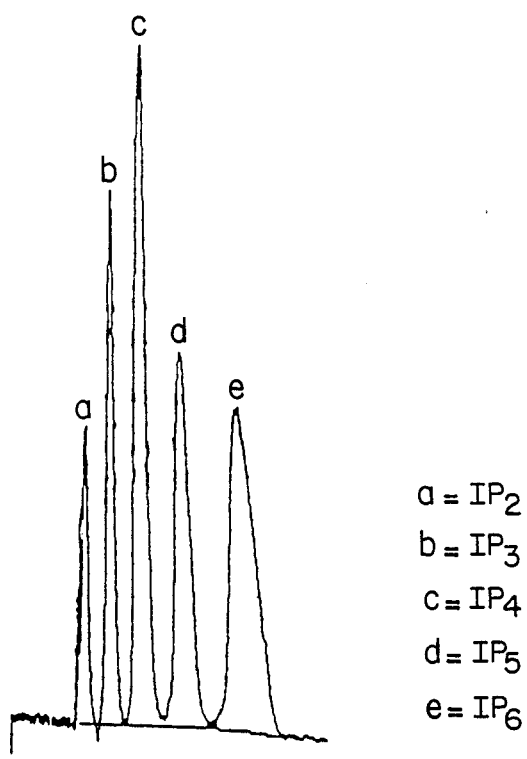

20 mg of the bariumsalt was converted to the acid form by addition of diluted hydrochloric acid and was analyzed by HPLC. The analysis method was calibrated with well-defined inositolphosphates. FIG. 11 shows the chromatoram. The fraction determined to be inositoltriphosphate was collected.

The H-NMR spectrum indicated a substantial number of someric products.

EXAMPLE 21

1.0 kg of rice bran, containing ca 1% inositolhexaphosphate ($IP_6$) was suspended in 10 l sodiumacetate buffer at pH 5 at 25° C. After 4 hours when 50% inorganic phosphorus had been released the slurry was extracted with an addition of 1 l 2M HCl. The suspension was shaken for 1 hour and subsequently centrifuged. The supernatant was neutralized to pH 7 with an aqueous solution of $Ca(OH)_2$. A precipitate was obtained when 5 l ethanol was added. The calciumsalt consisting of a composition of different inositolphosphates was centrifuged, dried and recrystalized. 20 mg of the recrystallized calciumsalt was converted to the acid form by addition of diluted hydrochloric acid and was analyzed by HPLC. The composition consisted of 40 % inositoltriphosphate of which 70% was D-myoinositol-1.2.6-triphosphate. The rest consisted of other inositolphosphates.

EXAMPLE 22

Characterization of different salts of D-myo-inositol-1.2.6-triphosphate 70 ml of the fraction with the phosphorus/inositol ratio of three to one obtained in Example 15 was divided in 7 portions. After pH adjustment with 0.1 M NaOH different positive ions in the chloride form was added, one ion to each portion. The salts used were $FeCl_3$, $MdCl_2$, $AlCl_3$, $KCl$, $NH_4Cl$, $(CH_3CH_2CH_2CH_2)_4N$ Cl and $C_6H_{13}NH_3Cl$ respectively.

After addition of 10 ml ethanol precipitates were formed. The salts were recrystalized and analyzed for the content of phosphorus, carbon, oxygen and metal after recrystallization. Table 1 below shows the composition of purified salts.

EXAMPLE 23

The effect of $IP_3$ on platelet aggregation after smoking in humans was studied Four young healthy male non-smokers received, on two occasions, a capsule containing 50 mg of $IP_3$ or 50 mg of a placebo. The $IP_3$ used was the Ca-salt of D-myoinositol-1.2.6-triphosphate. Neither subject nor investigator knew whether the subject had recieved $IP_3$ or placebo.

Two hours after ingestion of the capsule, a blood sample was obtained. The subject then smoked two cigaretts in rapid succession. A second blood sample was obtained after smoking. The aggregation responses of the platelets to ADP and collagen in the two samples were determined, using essentially the same procedure as in Example 1. The results are expressed as change in aggregation from the pre-smoking to the post-smoking sample. A positive sign indicates that aggregation was stronger after smoking.

| Aggregating agent | Concentration of aggregating agent | $IP_3$ | Placebo | Difference between $IP_3$ and placebo |
|---|---|---|---|---|
| ADP | 0.5 mmol | +1.5 | +7.25 | 5.85 |
| " | 1 mmol | −1.5 | +0.25 | 1.75 |
| " | 2.5 mmol | −1.5 | 0 | 1.5 |
| " | 5 mmol | −2.5 | −0.75 | 1.75 |
| Collagen | 0.5 mg | +5.15 | +12.25 | 6.5 |
| " | 1 mg | −8.25 | +1.75 | 10.0 |
| " | 2.5 mg | −3.75 | 0 | 3.75 |
| " | 5 mg | −1.5 | −0.25 | 1.25 |

In the placebo group, smoking caused an increase in aggregation, which was most marked at low concentrations of aggregation agents. In all cases this effect was counteracted by $IP_3$. Thus $IP_3$ prevents increase of platelet aggregation caused by smoking. EXAMPLE 24

Mice, 10 in each group, were injected intraperitoneally with $IP_3$ (Na-salt of D-myo-inositol-1.2.6-triphosphate) in three dose levels or with physiological saline. 30 minutes after this injection, all mice except one control group received an intravenous injection of alloxan, 50 mg/kg in saline.

The animals were starved for 12 hours before, and one hour after the alloxan injection. 72 hours after the alloxan injection, a blood sample from the mice were analyzed with respect to glucose level. The results were as follows:

| Dose of $IP_3$ mg/kg | Dose of alloxan mg/kg | Blood glucose |
|---|---|---|
| 0 | 0 | 216 |
| 0 | 50 | 864 |
| 800 | 50 | 857 |
| 1600 | 50 | 677 |

Alloxan causes diabetes and increased blood glucose level by promotion free radical reactions in the insulin producing cells. With $IP_3$ there was a dose-dependent decrease in blood glucose levels, and the highest dose gave some protection to the alloxan.

TABLE 1

| | Chemical formulations of different salts of $IP_3$. | | | | | | |
|---|---|---|---|---|---|---|---|
| | | Elementary analysis | | | | | |
| Compound | | Me % | C % | O % | P % | N % | Formula |
| Calciumsalt of 1.2.6-$IP_3$ | Ca: | 22.0 | 14.1 | 44.2 | 17.1 | — | $Ca_3IP_3$ |
| Calciumsalt of 1.3.4-$IP_3$ | Ca: | 21.4 | 13.8 | 42.9 | 16.3 | — | $Ca_3IP_3$ |
| Calciumsalt of 1.2.3-$IP_3$ | Ca: | 22.7 | 12.9 | 45.6 | 18.2 | — | $Ca_3IP_3$ |
| Calciumsalt of 1.2.5-$IP_3$ | Ca: | 23.2 | 13.3 | 44.7 | 16.9 | — | $Ca_3IP_3$ |
| Zincsalt of 1.2.6-$IP_3$ | Zn: | 31.5 | 12.1 | 38.2 | 14.7 | — | $Zn_3IP_3$ |
| Sodiumsalt of 1.2.6-$IP_3$ | Na: | 23.1 | 12.8 | 44.6 | 15.8 | — | $Na_6IP_3$ |
| Ironsalt of 1.2.6-$IP_3$ | Fe: | 21.5 | 13.1 | 43.4 | 18.2 | — | $Fe_2IP_3$ |

TABLE 1-continued

Chemical formulations of different salts of $IP_3$.

| Compound | | Me % | C % | O % | P % | N % | Formula |
|---|---|---|---|---|---|---|---|
| Potassium, magnesiumsalt of 1.2.6-$IP_3$ | K:<br>Mg: | 27.5<br>3.8 | 11.3 | 38.7 | 14.1 | — | $K_4Mg\ IP_3$ |
| Magnesiumsalt of 1.2.6.-$IP_3$ | Mg: | 15.8 | 16.0 | 50.8 | 18.9 | — | $Mg_3IP_3$ |
| Aluminiumsalt of 1.2.6-$IP_3$ | Al: | 12.6 | 15.8 | 53.3 | 21.2 | — | $Al_2IP_3$ |
| Ammoniumsalt of 1.2.6-$IP_3$ | | — | 13.1 | 47.8 | 16.9 | 15.6 | $(NH_4)_6IP_3$ |
| Tetrabutyl ammoniumsalt of 1.2.6-$IP_3$ | | — | 57.0 | 20.1 | 7.8 | 3.5 | $[(CH_3(CH_2)_3)_4N]_3H_3IP_3$ |
| Cyclohexylammoniumsalt of 1.2.6-$IP_3$ | | — | 39.5 | 35.1 | 12.6 | 6.2 | $[(C_6H_3NH_3]_3H_3IP_3$ |

EXAMPLE 25

Determination of pKa-values for inositoltriphosphates

Figure 12:
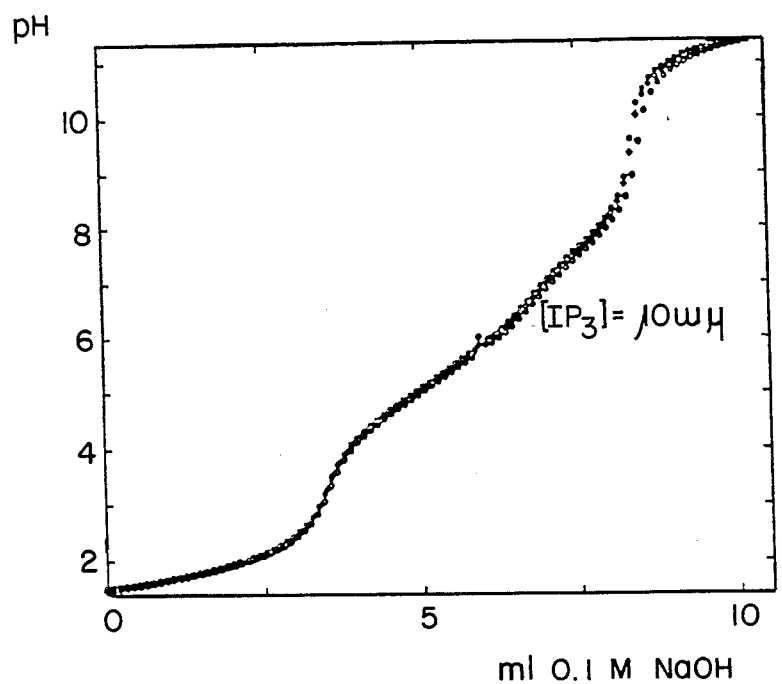

A solution consisting of 10 mM D-myo-inositol-1.2.6-triphosphate in 1 M NaCl was titrated with a 0.1M solution of NaOH. The pH during the titration was measured with an electrod. FIG. 12 shows the pH versus volume NaOH.

From the titration curve obtained, utilization of Nernst law and equilibrium equations the following pKa-values could be determined.

$$pKa_1=2.95\ pKa_2=5.64\ pKa_3=6.01\ pKa_4=7.88$$

Conclusion from the look of the curve is that $pKa_5$ and $pKa_6$ should have a value above 11.

Figure 13:
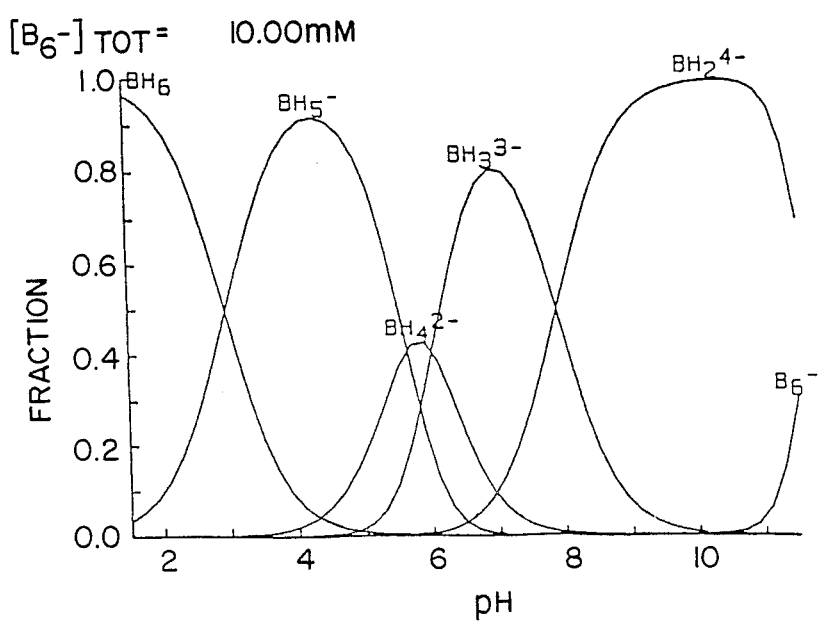

Utilizing the calculated pKa-value a fraction diagram showing the different protonated forms of $IP_3$ as a function of pH was made (FIG. 13).

EXAMPLE 25A

Figure 14:
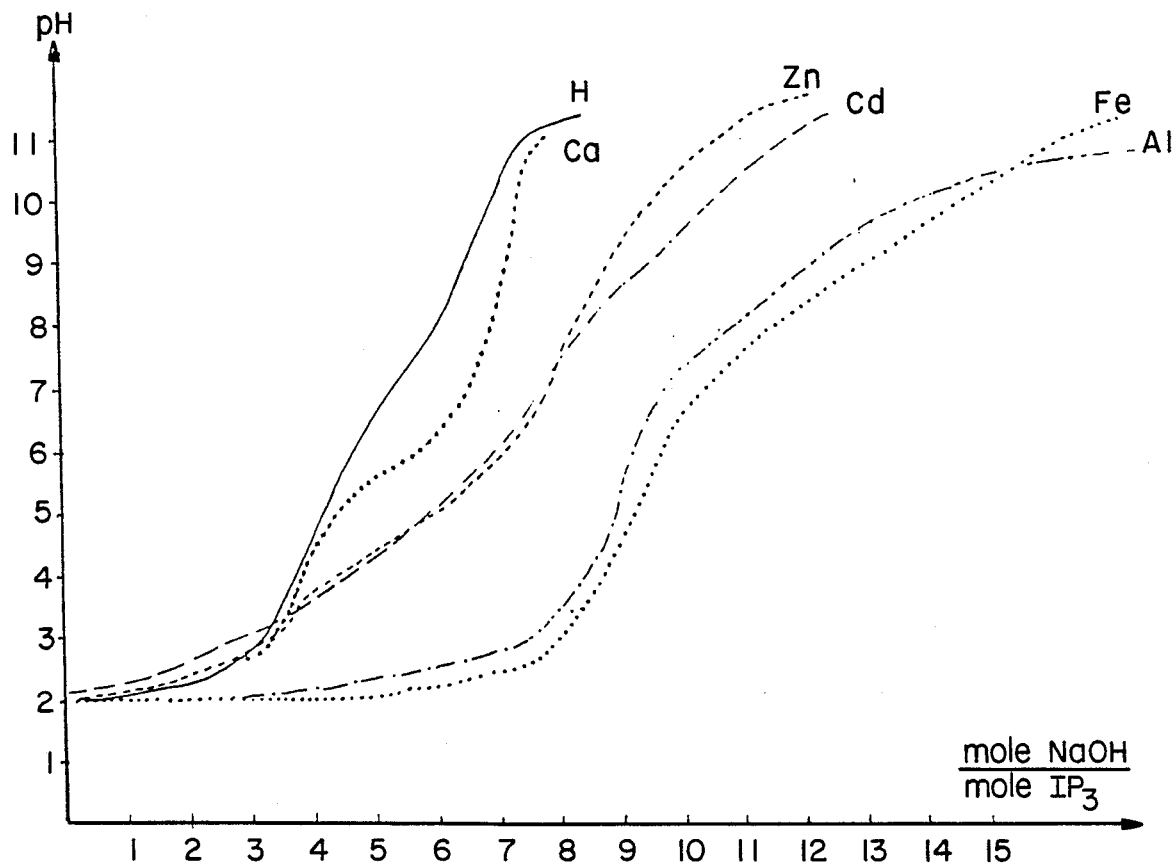

Determination of relative binding constants of inositol triphosphates with calcium, zinc, cadmium, iron and aluminium respectively A solution consisting of 4 mM D-myo-inositol-1.2.6-tripohsphate was titrated with 0.1M NaOH in presence of 12 mM calcium, zinc, cadmium, iron and aluminium respectively. A greater tendency to formation of an inositoltriphosphate—metal-complex results in lowering the pH at a certain amount NaOH added. As can be seen in FIG. 14 the metal binding constants of $IP_3$ increase in the following order:

$$Ca<Zn<Cd<Fe<Al$$

EXAMPLE 26

A 0.5 gram quantity of D-chiro-inositol was dissolved in 1 ml phosphoric acid at 60° C. 20 g polyphosphoric was added and the mixture was heated to 150° C. under vacuum for 6 hours. The mixture was diluted with water to a volume of 200 ml and passed through an ion-exchange column (Dowex 1, chloride form, 25 mm×250 mm) and eluted with a linear gradient of hydrochloric acid (0–2.0 N HCl).

The content of the peak with the ratio of phosphorus to inositol of six to one was precipitated by addition of calciumhydroxide. The precipitate was filtered, washed and mixed with 10 ml of a cation-exchange resin to give the acid form of the inositolhexaphosphate. After neutralization with sodium hydroxide and freezedrying the sodiumsalt of D-chiro-inositolhexaphosphate was obtained.

EXAMPLE 27

A 0.8 gram quantity of the sodium salt of D-chiro-inositolhexaphosphate produced according to Example 26 was dissolved in 300 ml sodium acetate buffer, pH 5.2. 1.3 gram wheat phytase (EC 3.1.3.26 0.015 U/mg from Sigma Chemical Co.) was added and the mixture was incubated at 38° C.

After the liberation of 50 % inorganic phosphorus the hydrolysis was stopped by adding ammonia to pH 12. The mixture containing D-chiro-inositolphosphates was passed through an ion-exchange column (Dowex 1 chloride form, 25 mm×250 mm) and eluted with a linear gradient of hydrochloric acid (0.-0.7 N Hcl).

The peak with the ratio of phosphorus to inositol of three to one was neutralized with 1.0M sodium hydroxide and freeze-dried.

Structural determination with NMR and IR showed the product to be D-chiro-inositoltriphosphate.

EXAMPLE 28

A 0.8 gram quantity of epi-inositol was dissolved in 1.5 ml of phosphoric acid at 60° C. 32 g polyphosphoric acid was added and the mixture was heated to 150° C. under vacuum for 6 hours. The mixture was diluted with water to a volume of 200 ml and passed through an ion-exchange column (Dowex 1, chloride form, 25×250 mm) and eluted with a linear gradient of hydrochloric acid (0–2.0 N Hcl).

The content of the peak with the ratio of phosphorus to inositol of six to one was precipitated by addition of calcium hydroxide. The precipitate was filtered, washed and mixed with 10 ml of a cation-exchange resin to give the acid form of the inositol hexaphosphate. After neutralization with sodium hydroxide and freeze-drying the sodium salt of epi-inositolhexaphosphate was obtained. EXAMPLE 29

A 1.2 gram quantity of the sodium salt of epi-inositolhexaphosphate produced according to Example 28 was dissolved in 500 ml sodium acetate buffer, pH 5.2 2.0 gram wheat phytase (EC 3.1.3.26, 0.015 U/mg from Sigma Chemical Co.) was incubated at 38° C.

After the liberation of 50% inorganic phosphorus the hydrolysis was stopped by adding ammonia to pH 12.

The mixture containing epi-inositolphosphates was passed through an ion-exchange column (Dowex 1, chloride form, 25 mm×250 mm) and eluted with a linear gradient of hydrochloric acid (0–0.7 N Hcl).

The peak with the ratio of phosphorus to inositol of three to one was neutralized with 1.0 M sodium hydroxide and freeze-dried.

Structural determination with NMR and IR showed the product to be epi-inositoltriphosphate.

I claim:

1. A product selected from the group consisting of a compound, a salt thereof and an acid thereof of an inositol triphosphate having the structural formula

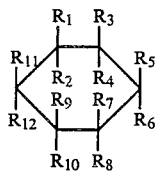

where
(a) three of $R_1$, $R_3$, $R_5$, $R_7$, $R_{10}$ and $R_{11}$ are hydroxyl and the remaining three are phosphate and $R_2$, $R_4$, $R_6$, $R_8$, $R_9$ and $R_{12}$ are hydrogen;
(b) three of $R_1$, $R_3$, $R_6$, $R_7$, $R_9$ and $R_{12}$ are hydroxyl and the remaining three are phosphate and $R_2$, $R_4$, $R_5$, $R_8$, $R_{10}$ and $R_{11}$ are hydrogen;
(c) three of $R_1$, $R_3$, $R_5$, $R_8$, $R_{10}$ and $R_{12}$ are hydroxyl and the remaining three are phosphate and $R_2$, $R_4$, $R_6$, $R_7$, $R_9$ and $R_{11}$ are hydrogen;
(d) three of $R_1$, $R_4$, $R_5$, $R_8$, $R_9$ and $R_{12}$ are hydroxyl and the remaining three are phosphate and $R_2$, $R_3$, $R_6$, $R_7$, $R_{10}$ and $R_{11}$ are hydrogen;
(e) three of $R_1$, $R_3$, $R_6$, $R_8$, $R_9$ and $R_{12}$ are hydroxyl and the remaining three are phosphate and $R_2$, $R_4$, $R_5$, $R_7$, $R_{10}$ and $R_{11}$ are hydrogen;
(f) three of $R_1$, $R_3$, $R_6$, $R_7$, $R_{10}$ and $R_{12}$ are hydroxyl and the remaining three are phosphate and $R_2$, $R_4$, $R_5$, $R_8$, $R_9$ and $R_{11}$ are hydrogen;
(g) three of $R_1$, $R_3$, $R_5$, $R_8$, $R_{10}$ and $R_{11}$ hydroxyl and the remaining three are phosphate and $R_2$, $R_4$, $R_6$, $R_7$, $R_9$ and $R_{12}$ are hydrogen; or
(h) three of $R_1$, $R_3$, $R_5$, $R_7$, $R_9$ and $R_{11}$ are hydroxyl and the remaining three are phosphate and $R_2$, $R_4$, $R_6$, $R_8$, $R_{10}$ and $R_{12}$ are hydrogen.

2. A product according to claim 1 wherein $R_5$, $R_7$ and $R_{10}$ are phosphate, $R_1$, $R_3$ and $R_{11}$ and hydroxyl and $R_2$, $R_4$, $R_6$, $R_8$, $R_9$ and $R_{12}$ are hydrogen.

3. A product according to claim 1 wherein $R_1$, $R_{10}$ and $R_{11}$ are phosphate, $R_3$, $R_5$ and $R_7$ are hydroxyl and $R_2$, $R_4$, $R_6$, $R_8$, ]and $R_{12}$ are hydrogen.

4. A product according to claim 1 wherein $R_1$, $R_3$ and $R_{11}$ are phosphate, $R_5$, $R_7$ and $R_{10}$ are hydroxyl and $R_2$, $R_4$, $R_6$, $R_8$, $R_9$ and $R_{12}$ are hydrogen.

5. A product according to claim 1 wherein $R_3$, $R_5$ and $R_7$ are phosphate, $R_1$, $R_{10}$ and $R_{11}$ are hydroxyl and $R_2$, $R_4$, $R_6$, $R_8$, $R_9$ and $R_{12}$ are hydrogen.

6. A product according to claim 1 wherein $R_3$, $R_7$ and $R_{10}$ are phosphate, $R_1$, $R_5$ and $R_{11}$ are hydroxyl and $R_2$, $R_4$, $R_6$, $R_8$, $R_9$ and $R_{12}$ are hydrogen.

7. A product according to claim 1 wherein $R_3$, $R_{10}$ and $R_{11}$ are phosphate, $R_1$, $R_5$ and $R_7$ are hydroxyl and $R_2$, $R_4$, $R_6$, $R_8$, $R_9$ and $R_{12}$ are hydrogen.

8. A product according to claim 1 wherein $R_1$, $R_3$ and $R_6$ are phosphate, $R_7$, $R_9$ and $R_{12}$ are hydroxyl and $R_2$, $R_4$, $R_5$, $R_8$, $R_{10}$ and $R_{11}$ are hydrogen.

9. A product according to claim 1 wherein $R_6$, $R_7$ and $R_9$ are phosphate, $R_1$, $R_3$ and $R_{12}$ are hydroxyl and $R_2$, $R_4$, $R_5$, $R_8$, $R_{10}$ and $R_{11}$ are hydrogen.

10. A product according to claim 1 wherein $R_3$, $R_5$ and $R_8$ are phosphate, $R_1$, $R_{10}$ and $R_{12}$ are hydroxyl and $R_2$, $R_4$, $R_6$, $R_7$, $R_9$ and $R_{11}$ are hydrogen.

11. A product according to claim 1 wherein $R_1$, $R_3$ and $R_{12}$ are phosphate, $R_5$, $R_8$ and $R_{10}$ are hydroxyl and $R_2$, $R_4$, $R_6$, $R_7$, $R_9$ and $R_{11}$ are hydrogen.

12. A product according to claim 1 wherein $R_1$, $R_3$ and $R_5$ are phosphate, $R_8$, $R_{10}$ and $R_{12}$ are hydroxyl and $R_2$, $R_4$, $R_6$, $R_7$, $R_9$ and $R_{11}$ are hydrogen.

13. A product according to claim 1 wherein $R_1$, $R_5$ and $R_8$ are phosphate, $R_3$, $R_{10}$ and $R_{12}$ are hydroxyl and $R_2$, $R_4$, $R_6$, $R_7$, $R_9$ and $R_{11}$ are hydrogen.

14. A product according to claim 1 wherein $R_1$, $R_5$ and $R_{12}$ are phosphate, $R_3$, $R_8$ and $R_{10}$ are hydroxyl and $R_2$, $R_4$, $R_6$, $R_7$, $R_9$ and $R_{11}$ are hydrogen.

15. A product according to claim 1 wherein $R_1$, $R_3$ and $R_{12}$ are phosphate, $R_6$, $R_8$ and $R_9$ are hydroxyl and $R_2$, $R_4$, $R_5$, $R_7$, $R_{10}$ and $R_{11}$ are hydrogen.

16. A product according to claim 1 wherein $R_1$, $R_3$ and $R_6$ are phosphate, $R_7$, $R_{10}$ and $R_{12}$ are hydroxyl and $R_2$, $R_4$, $R_5$, $R_8$, $R_9$ and $R_{11}$ are hydrogen.

17. A product according to claim 1 wherein $R_4$, $R_5$ and $R_8$ are phosphate, $R_1$, $R_9$ and $R_{12}$ are hydroxyl and $R_2$, $R_3$, $R_6$, $R_7$, $R_{10}$ and $R_{11}$ are hydrogen.

18. A product according to claim 1 wherein $R_3$, $R_5$ and $R_8$ are phosphate, $R_1$, $R_{10}$ and $R_{11}$ are hydroxyl and $R_2$, $R_4$, $R_6$, $R_7$, $R_9$ and $R_{12}$ are hydrogen.

19. A product according to claim 1 wherein $R_1$, $R_3$ and $R_5$ are phosphate, $R_8$, $R_{10}$ and $R_{11}$ are hydroxyl and $R_2$, $R_4$, $R_6$, $R_7$, $R_9$ and $R_{12}$ are hydrogen.

20. A product according to claim 1 wherein $R_1$, $R_3$ and $R_5$ are phosphate, $R_7$, $R_9$ and $R_{11}$ are hydroscyl and $R_2$, $R_4$, $R_6$, $R_8$, $R_{10}$ and $R_{12}$ are hydrogen.

21. A product selected from the group consisting of a compound, a salt thereof and an acid thereof of an inositol triphosphate having the structural formula

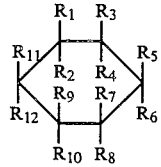

where
(a) $R_1$, $R_3$ and $R_{12}$ are phosphate; $R_5$, $R_8$ and $R_9$ are hydroxyl; and $R_2$, $R_4$, $R_6$, $R_7$, $R_{10}$ and $R_{11}$ are hydrogen;
(b) $R_1$, $R_3$ and $R_8$ are phosphate; $R_5$, $R_9$ and $R_{12}$ are hydroxyl; and $R_2$, $R_4$, $R_6$, $R_7$ and $R_{10}$ and $R_{11}$ are hydrogen;
(c) $R_3$, $R_5$ and $R_{12}$ are phosphate; $R_1$, $R_8$, and $R_9$ are hydroxyl; and $R_2$, $R_4$, $R_6$, $R_7$, $R_{10}$ and $R_{11}$ are hydrogen;
(d) $R_1$, $R_5$ and $R_9$ are phosphate; $R_3$, $R_8$ and $R_{12}$ are hydroxyl; and $R_2$, $R_4$, $R_6$, $R_7$, $R_{10}$ and $R_{11}$ are hydrogen;
(e) $R_1$, $R_3$ and $R_9$ are phosphate; $R_5$, $R_8$ and $R_{12}$ are hydroxyl; and $R_2$, $R_4$, $R_6$, $R_7$, $R_{10}$ and $R_{11}$ are hydrogen;
(f) $R_1$, $R_8$ and $R_9$ are phosphate; $R_3$, $R_5$, and $R_{12}$ are hydroxyl; and $R_2$, $R_4$, $R_6$, $R_7$, $R_{10}$ and $R_{11}$ are hydrogen;

(g) $R_1$, $R_8$ and $R_{12}$ are phosphate; $R_3$, $R_5$ and $R_9$ are hydroxyl; and $R_2$, $R_4$, $R_6$, $R_7$, $R_{10}$ and $R_{11}$ are hydrogen;

(h) $R_5$, $R_8$ and $R_{12}$ are phosphate; $R_1$, $R_3$ and $R_9$ are hydroxyl; and $R_2$, $R_4$, $R_6$, $R_7$, $R_{10}$ and $R_{11}$ are hydrogen;

(i) $R_1$, $R_9$ and $R_{12}$ are phosphate; $R_3$, and $R_8$ are hydroxyl; and $R_2$, $R_4$, $R_6$, $R_7$, $R_{10}$ and $R_{11}$ are hydrogen;

(j) $R_5$, $R_8$ and $R_9$ are phosphate; $R_1$, $R_3$ and $R_{12}$ are hydroxyl; $R_2$, $R_4$, $R_6$, $R_7$, $R_{10}$ and $R_{11}$ are hydroge;

(k) $R_3$, $R_8$ and $R_9$ are phosphate; $R_1$, $R_5$ and $R_{12}$ are hydroxyl; and $R_2$, $R_4$, $R_6$, $R_7$, $R_{10}$ and $R_{11}$ are hydrogen;

(l) $R_3$, $R_8$ and $R_{12}$ are phosphate; $R_1$, $R_5$ and $R_9$ are hydroxyl; and $R_2$, $R_4$, $R_6$, $R_7$, $R_{10}$, and $R_{11}$ are hydrogen; or (m) $R_8$, $R_9$ and $R_{12}$ are phosphate; $R_1$, $R_3$ and $R_5$ are hydroxyl; and $R_2$, $R_4$, $R_6$, $R_7$, $R_{10}$ and $R_{11}$ are hydrogen.

* * * * *

UNITED STATES PATENT AND TRADEMARK OFFICE
CERTIFICATE OF CORRECTION

PATENT NO. : 4,851,560                       Page 1 of 2

DATED : July 25, 1989

INVENTOR(S) : Matti Siren

It is certified that error appears in the above-identified patent and that said Letters Patent is hereby corrected as shown below:

In the Abstract, section (d): "three or" should read as --three of--

Column 1, line 38: after "high" add --an--

Column 8, line 44: "$R_{10}$ and $R_{10}$ and $R_{12}$" should read as --$R_{10}$ and $R_{12}$--

Column 10, line 34: "1.2.8-triphosphate," should read as --1.2.6-triphosphate,--

Column 11, lines 29-30: "solution of 100 ml ethanol." should read as --solution of $Ca(OH)_2$. The calciumsalt was precipitated by the addition of 100 ml ethanol.--

Column 11, line 46: "1.2.4-triphosphate" should read as --1.3.4-triphosphate--

Column 11, lines 66-67: "100 ethanol." should read as --100 ml ethanol.--

UNITED STATES PATENT AND TRADEMARK OFFICE
CERTIFICATE OF CORRECTION

PATENT NO.  : 4,851,560
DATED       : July 25, 1989
INVENTOR(S) : Matti Siren

It is certified that error appears in the above-identified patent and that said Letters Patent is hereby corrected as shown below:

Column 12, line 20: "D-mayo-inositol" should read as --D-myo-inositol--

Column 15, line 34: "MdCl$_2$," should read as --MgCl$_2$,--

Column 17, line 57: after "polyphosphoric" add --acid--

Column 19, line 49, Claim 2: "R$_{11}$ and" should read as --R$_{11}$ are--

Column 19, line 53, Claim 3: "[and" should read as -- R$_9$ and--.

Column 20, line 36, Claim 20: "hydrosyl" should read as --hydroxyl--

Column 21, line 9, Claim 21: "R$_3$, =and R$_8$" should read as --R$_3$, R$_5$ and R$_8$--

Signed and Sealed this

Nineteenth Day of May, 1992

*Attest:*

DOUGLAS B. COMER

*Attesting Officer*   *Acting Commissioner of Patents and Trademarks*